US009469653B2

(12) United States Patent
Lee et al.

(10) Patent No.: US 9,469,653 B2
(45) Date of Patent: Oct. 18, 2016

(54) PHARMACEUTICAL COMPOSITIONS FOR PREVENTING OR TREATING DEGENERATIVE BRAIN DISEASE AND METHOD OF SCREENING THE SAME

(71) Applicant: KOREA INSTITUTE OF SCIENCE AND TECHNOLOGY, Seoul (KR)

(72) Inventors: Changjoon Justin Lee, Seoul (KR); Seonmi Jo, Suncheon-si (KR); Boeun Yoon, Seoul (KR); Hyunah Choo, Seoul (KR); Ji Yoon Kim, Seoul (KR); Daesoo Kim, Daejeon (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 334 days.

(21) Appl. No.: 14/164,616

(22) Filed: Jan. 27, 2014

(65) Prior Publication Data

US 2014/0142089 A1    May 22, 2014

Related U.S. Application Data

(62) Division of application No. 13/588,383, filed on Aug. 17, 2012, now abandoned.

(30) Foreign Application Priority Data

Aug. 18, 2011  (KR) .................. 10-2011-0082345
Aug. 16, 2012  (KR) .................. 10-2012-0089402

(51) Int. Cl.
| | | |
|---|---|---|
| C07D 513/04 | (2006.01) | |
| G01N 33/68 | (2006.01) | |
| C07D 498/04 | (2006.01) | |
| G01N 33/50 | (2006.01) | |
| G01N 33/94 | (2006.01) | |

(52) U.S. Cl.
CPC ........... *C07D 498/04* (2013.01); *C07D 513/04* (2013.01); *G01N 33/5058* (2013.01); *G01N 33/6896* (2013.01); *G01N 33/9426* (2013.01); *C12N 2503/02* (2013.01); *G01N 2800/2814* (2013.01); *G01N 2800/302* (2013.01)

(58) Field of Classification Search
None
See application file for complete search history.

(56) References Cited

FOREIGN PATENT DOCUMENTS

| KR | 10-1154538 | 6/2012 |
|---|---|---|
| WO | WO 98/43094 | 10/1998 |
| WO | WO 99/11758 | 3/1999 |
| WO | WO 2005/106038 A3 | 11/2005 |
| WO | WO 2006/000324 A2 | 1/2006 |
| WO | WO 2009/096612 A1 | 8/2009 |
| WO | WO 2010/051196 A1 | 5/2010 |
| WO | WO 2010/077068 A2 | 7/2010 |
| WO | WO 2010/077068 A3 | 7/2010 |
| WO | WO 2011/025230 A2 | 3/2011 |
| WO | WO 2011/025230 A3 | 3/2011 |
| WO | WO 2011/025230 A9 | 3/2011 |

OTHER PUBLICATIONS

Japanese Office Action mailed Jun. 18, 2013 in corresponding Japanese Application No. 2012-181633.
Korean Office Action issued Sep. 2, 2013 in corresponding Korean Patent Application No. 10-2012-0089402.
Maragakis et al. "*Mechanisms of Disease: astrocytes in neurodegenerative disease*" Nature Clinical Practice Neurology, vol. 2, No. 12, Dec. 2006. pp. 679-689.
Clarkson et al. 2010 "Reducing excessive GABAergic tonic inhibition promotes post-stroke functional recover" Nature 468 (7321):305-309.
Lee et al. 2010 "Channel-Mediated Tonic GABA release from glia" Science 330:790-796.
Mallajosyula et al. 2008 "MAO-B elevation in mouse brain astrocytes results in parkinsons pathology" PLoS one 3(2):e1616.
Rafii and Aisen 2009 "Recent developments in Alheimer's disease therapeutics" BMC Medicine 7:7.
US. Office Action issued Sep. 30, 2013 in copending U.S. Appl. No. 13/588,383.
Cope et al., Abstract of "Enhanced tonic $GABA_A$ inhibition in typical absence epilepsy", *Nature Medicine*, 2009, 3 pp., vol. 15, No. 12.
Korean Notice of Allowance mailed Aug. 11, 2014, in corresponding Korean Patent Application No. 10-2012-0089402.

*Primary Examiner* — Adam M Weidner
(74) *Attorney, Agent, or Firm* — Goldilocks Zone IP Law

(57) ABSTRACT

A pharmaceutical composition for preventing or treating a degenerative brain disease, and a method of screening a material for preventing or treating a degenerative brain disease. The method may effectively screen a prophylactic or therapeutic candidate material for preventing or treating a degenerative brain disease. A variety of degenerative brain diseases may be effectively prevented or treated using the pharmaceutical composition including a screened material for preventing or treating a degenerative brain disease.

2 Claims, 16 Drawing Sheets
(14 of 16 Drawing Sheet(s) Filed in Color)

PHARMACEUTICAL COMPOSITIONS FOR PREVENTING OR TREATING DEGENERATIVE BRAIN DISEASE AND METHOD OF SCREENING THE SAME

CROSS-REFERENCE TO RELATED APPLICATIONS

This application is a divisional of U.S. application Ser. No. 13/588,383, filed Aug. 17, 2012, which claims the benefit of Korean Patent Application No. 10-2011-0082345, filed on Aug. 18, 2011, and Korean Patent Application No. 10-2012-0089402, filed on Aug. 16, 2012, in the Korean Intellectual Property Office, the disclosures of which are incorporated herein in their entirety by reference.

BACKGROUND

1. Field

The present disclosure relates to a pharmaceutical composition for diagnosing or treating a degenerative brain disease, and a method of screening the same.

2. Description of the Related Art

Degenerative brain diseases, including Alzheimer's disease, mostly cause memory and cognitive dysfunction and behavioral problems. In particular, Alzheimer's disease is a chronic disease gradually worsening over several years, which causes severe emotional distress to the patient and family, and huge medical expenses. Drugs developed so far for treatment of Alzheimer's disease temporarily relieve symptoms only, and thus, there is a high demand for fundamental treatment or progress suppression of the disease.

For example, a main target in developing a therapeutic agent for Alzheimer's disease has been neurotransmitters found in Alzheimer's disease, such as cholinergic neurons, and thus, cholinesterase inhibitors (such as Aricept, Exelon, Reminyl, or the like) are commercially available. A recently FDA-approved medication called memantine, which is a glutamate receptor antagonist, is also developed with a representative neurotransmitter glutamate as a target. However, these drugs basically cannot block the progression of the disease itself, and in recent years, there has been active research into the development of drugs targeting β-amyloid (Aβ), which forms amyloid plaques as a key component found in Alzheimer's disease, to suppress a β- or γ-secretase that are important in the generation of the β-amyloid (Aβ), or to decompose the generated β-amyloid (Aβ). However, this targeting on a normal protein present in the human body may inhibit a normal function of the protein, leading to a side effect.

Therefore, there is a demand for a prophylactic or therapeutic pharmaceutical composition targeting on new proteins associated with a variety of degenerative brain diseases, based on existing technologies.

SUMMARY

The present disclosure provides a method of screening a prophylactic or therapeutic candidate material for preventing or treating a degenerative brain disease.

The present disclosure also provides a prophylactic or therapeutic pharmaceutical composition for preventing or treating a degenerative brain disease.

According to an aspect of the present disclosure, there is provided a method of screening candidate materials for preventing or treating a degenerative brain disease, the method including: (a) contacting a target assay sample to a reactive astrocyte; and (b) determining if the target assay sample reduces a concentration of γ-aminobutylic acid (GABA) in the reactive astrocyte or reduce release of GABA from the reactive astrocyte, wherein the target assay sample is determined as a candidate material for diagnosing or treating a degenerative brain disease if the target assay sample is determined to reduce the concentration of GABA in the reactive astrocyte or to reduce the release of GABA from the reactive astrocyte.

According to an aspect of the present disclosure, there is provided a method of screening candidate materials for preventing or treating a degenerative brain disease, the method including: (a) contacting a target assay sample to a reactive astrocyte; and (b) measuring an expression amount of a gene encoding a monoamine oxidase B (MAO-B) in the reactive astrocyte, or an amount or activity of an MAO-B protein, wherein the target assay sample is determined as a candidate material for diagnosing or treating a degenerative brain disease if the expression amount of the gene encoding the MAO-B, or the amount or activity of the MAO-B protein is found to be down-regulated.

According to an aspect of the present disclosure, there is provided a method of screening candidate materials for preventing or treating a degenerative brain disease, the method including: (a) contacting a target assay sample to a reactive astrocyte; and (b) determining a subcellular localization pattern of a bestrophine 1 channel in the reactive astrocyte, wherein the target assay sample is determined as a candidate material for diagnosing or treating a degenerative brain disease if the subcellular localization pattern of the bestrophine 1 channel is determined to be changed from a cell body and a main process Into a microdomain direction.

According to an aspect of the present disclosure, there is provided a method of screening candidate materials for preventing or treating a degenerative brain disease, the method including: (a) contacting a target assay sample to a reactive astrocyte; and (b) measuring an expression amount of a gene encoding Best 1 in the reactive astrocyte or an amount or activity of Best 1 protein, wherein the target assay sample is determined as a candidate material for preventing or treating the degenerative brain disease if the expression amount of the gene encoding Best 1, or the amount or activity of the Best 1 protein is found to be down-regulated.

According to an aspect of the present disclosure, there is provided a method of screening candidate materials for preventing or treating a degenerative brain disease, the method including: (a) contacting a target assay sample to a reactive astrocyte; and (b) measuring an expression amount of a gene encoding a γ-aminobutylic acid (GABA) transaminase in the reactive astrocyte, or an amount or activity of a GABA transaminase protein, wherein the target assay sample is determined as a candidate material for preventing or treating the degenerative brain disease if the expression amount of the gene encoding the GABA transaminase, or the amount or activity of the GABA transaminase protein is found to be up-regulated.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features and advantages of the present disclosure will become more apparent by describing in detail exemplary embodiments thereof with reference to the attached drawings in which.

DETAILED DESCRIPTION

Figure 1:
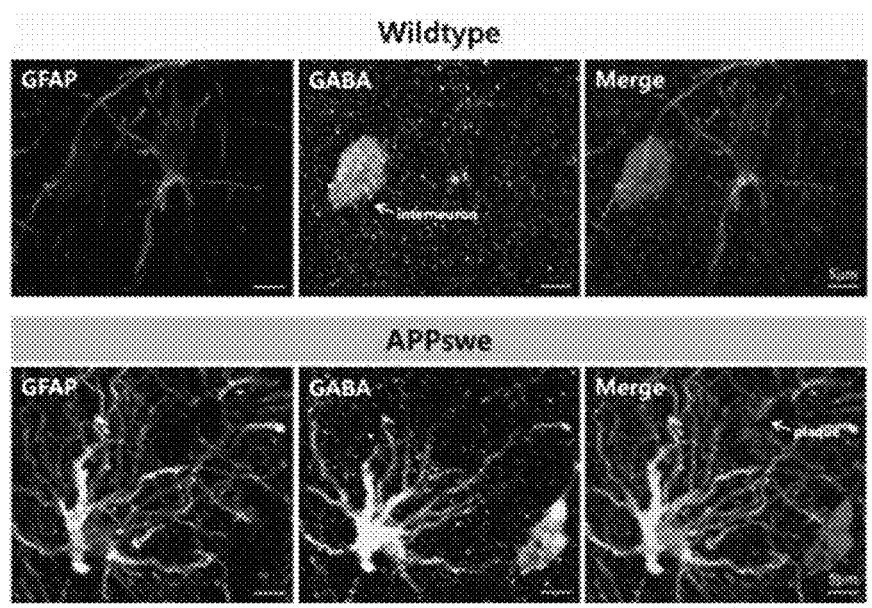
FIG. 1 shows confocal fluorescent images of hippocampal reactive astrocytes of a mouse model of Alzheimer's disease, illustrating γ-aminobutylic acid (GABA) in the hippocampal reactive astrocyte.

As used herein, the term "and/or" includes any and all combinations of one or more of the associated listed items. Expressions such as "at least one of," when preceding a list of elements, modify the entire list of elements and do not modify the individual elements of the list.

The inventors of the present disclosure made efforts to research and develop drugs for preventing an onset of degenerative brain diseases, including Alzheimer's disease, or treating the same, and found an increase in concentration of gamma-aminobutyric acid (GABA) as a neurotransmitter in hippocampal reactive astrocytes using an animal model of Alzheimer's disease, along with a cause thereof, such as increased expression of MAO-B as an essential enzyme involved in the production of GABA or the reduced expression of GABA transaminase. The inventors also found a change in subcellular localization pattern of bestrophine 1 channel through which GABA can pass or an increased expression of bestrophine 1 in the reactive astrocytes.

The present disclosure relates to a method of screening a prophylactic or therapeutic material for preventing or treating a degenerative brain disease, the material reducing a concentration of GABA in reactive astocytes, and in particular, the method targeting MAO-B, bestrophine 1 channel, or a GABA transaminases in association with degenerative brain diseases. Thus, this novel use of the proteins as a target in preventing or treating neuroegenerative diseases is based on the inventors' findings that hippocampal reactive astrocytes in a mouse model of Alzheimer's disease have increased expression of MAO-B, and a reduced expression of GABA transaminases, relative to a normal mouse model, so that a concentration of GABA in the hippocampal reactive astrocytes is increased, a subcellular localization pattern of bestrophine 1 channel is changed, and a degree of expression of bestrophine 1 is increased, leading to secretion of GABA out of the reactive astrocytes, and thus, generates tonic GABA outside the reactive astrocytes.

Tonic GABA, in the form of being bound to a tonic GABA receptor in nerve cells, allows chloride ions (Cl—) to enter neurons. This interferes with normal neuronal signaling by lowering a resting membrane potential of nerve cells. Absence epilepsy is known as a disease in which neuronal signaling is inhibited by tonic GABA (David W. Cope, Giuseppe Di Giovanni, Sarah J. Fyson, Gergely Orbán, Adam C. Errington, Magor L. Lörincz, Timothy M. Gould, David A. Carter, and Vincenzo Crunelli, Nat. Med., 2009, 15(12); 1392-1398). In a stroke, inhibiting tonic GABA is known to facilitate nerve recovery (Andrew N. Clarkson, Ben S. Huang, Sarah E. MacIsaac, Istvan Mody, and S. Thomas Carmichael, Nature, 2010, 468; 305-309). Furthermore, reportedly, inhibiting a hippocampus-specific receptor of tonic GABA may improve the memory and cognitive abilities (G. R. Dawson, K. A. Maubach, N. Collinson, M. Cobain, B. J. Everitt, A. M. MacLeod, H. I. Choudhury, L. M. McDonald, G. Pillai, W. Rycroft, A. J. Smith, F. Sternfeld, F. D. Tattersall, K. A. Wafford, D. S. Reynolds, G. R. Seabrook, and J. R. Atack, JPET, 2006, 316(3):1335-1345; H. Lal, B. Kumar, and M. J. Forster, The FASEB Journal, 1988, 2(11:2707-2711).

A degenerative brain disease collectively refers to any brain disease occurring from a degenerative change in nerve cells of the central nervous system. The causes of degenerative brain diseases are mostly unknown, and the disease has slow onset and continuously progresses via selective intrusion into associated nerve systems. In some embodiments, for example, the degenerative brain disease is selected from the group consisting of Alzheimer's disease, mild cognitive impairment, vascular dementia, frontotemporal dementia, Louis body dementia, Creutzfeld-Jakob disease, traumatic head injuries, syphilis, acquired immune deficiency syndrome (AIDS) and other viral infections, brain abscess, brain tumor, sclerosis, dementia in metabolic disease, hypoxia, Parkinson's disease, Huntington's disease, Pick's disease, amyotrophic lateral sclerosis (ALS), epilepsy, ischemia, stroke, attention deficit hyperactivity disorder (ADHD), schizophrenia, depression, manic-depression, stress disorder, spinal cord injury, and myelitis.

According to the method of the present disclosure, a method of screening a pharmaceutical composition for preventing or treating a degenerative brain disease includes contacting a target sample to be assayed and a reactive astrocyte. In some embodiments, the reactive astrocyte may originate from a brain tissue of an animal model with a brain injury, a brain tissue of a virus-infected animal, a brain tissue of an animal model with Parkinson's disease, or a brain tissue of an animal model with Alzheimer's disease. The animal model may originate from mammals, and in some embodiments, may originate from rodents such as mice or rats, or primates such as monkeys, but is not limited thereto. In some embodiments, the brain tissue may be the hippocampus, corpus striatum, substantia nigra pars compacta, or thalamic nuclei, but is not limited thereto.

The term "sample" used with regard to the screening method refers to a unidentified candidate material to be screened that is tested to determine if it may reduce a concentration of GABA in reactive astrocytes or may reduce release of GABA from the reactive astrocytes. A mechanism to reduce the concentration of GABA or the release of GABA may be, for example, as follows: i) increased expression of a gene encoding MAO-B in the reactive astrocytes, increased amount of the MAO-B protein, or increased activity of the MAO-B protein, ii) increased expression of a gene encoding Best 1, increased amount or activity of the Best 1 protein in the reactive astrocytes, or a shift in subcellular localization pattern of the bestrophine 1 channel in the reactive astrocytes from a microdomain direction into a cell body and a main process, or iii) a reduced expression of a gene encoding a GABA transaminase in the reactive astrocytes, reduced amount of the GABA transaminase protein, or reduced activity of the GABA transaminase protein. Non-limiting examples of the sample are chemical materials, nucleotides, anti-sense-RNA, short hairpin RNA (shRNA), small interfering RNA (siRNA), and natural extracts.

Subsequently, it is determined if a sample to be assayed may reduce the concentration of GABA in treated reactive astrocytes using the following three methods:

i) An expression amount of a gene encoding MAO-B in the reactive astrocytes, an amount of the MAO-B protein, or activity of the MAO-B protein is determined. As a result, if the expression amount of the gene encoding the MAO-B, or the amount or activity of the MAO-B protein is found to be down-regulated, the target assay sample may be determined as a candidate prophylactic or therapeutic material for a degenerative brain disease.

ii) An expression amount of a gene encoding Best 1 in the reactive astrocytes or an amount or activity of the Best 1 protein is measured. As a result, if the expression amount of the gene encoding Best 1, or the amount or activity of the Best 1 protein is found to be down-regulated, the target assay sample may be determined as a candidate material for preventing or treating a degenerative brain disease.

iii) A subcellular localization pattern of the bestrophine 1 channel in the reactive astrocytes is determined. As a result, the target assay sample may be determined as a candidate prophylactic or therapeutic material for preventing or treating a degenerative brain disease if the subcellular localization pattern of the bestrophine 1 channel is determined to be changed from a cell body and a main process into a microdomain direction.

iv) An expression amount of a gene encoding a GABA transaminase in the reactive astrocyte, or an amount or activity of a GABA transaminase protein may be determined. As a result, if the expression amount of the gene encoding the GABA transaminase, or the amount or activity of the GABA transaminase protein is found to be up-regulated, the target assay sample may be determined as a candidate prophylactic or therapeutic material for preventing or treating a degenerative brain disease.

The change in expression amount of the gene encoding the protein (MAO-B, Best 1, or GABA transaminase) may be measured by any of a variety of methods, for example, via hybridization reaction using RT-PCR, northern blotting or a cDNA microarray, or via in situ hybridization reaction. For example, when using an RT-PCR protocol, after separation of a total RNA from treated cells of a sample, a first chain cDNA is prepared using an oligo dT primer and a reverse transcriptase. Subsequently, PCR is performed using the first chain cDNA as a template and a set of primers specific to the genes encoding the proteins. Afterward, a PCR amplification product is subjected to electrophoresis to analyze bands from the electrophoresis, thereby measuring a change in the expression amount of the specific protein-encoding gene.

The change in amount of the proteins (MAO-B, bestrophine 1 channel, or GABA transaminase) or in subcellular localization pattern may be measured using any of a variety of methods. For example, the change in amount of MAO-B, Best 1, or GABA transaminase may be identified using immunohistochemistry, radioactive immunoassay, radioactive immunoprecipitation, immunoprecipitation, western blotting, ELISA, capture-ELISA, or sandwich assay, but is not limited thereto. The shift in subcellular localization pattern of the protein may be identified using, but not limited to, immunohistochemistry and transmission electron microscopy (TEM). The change in activity of the proteins may be measured using an in vitro enzyme activity assay, which is known in the art.

According to another aspect of the present disclosure, a pharmaceutical composition for preventing or treating a degenerative brain disease includes an effective component that is a material reducing a concentration of GABA in a reactive astrocyte.

According to still another aspect of the present disclosure, a pharmaceutical composition for preventing or treating a degenerative brain disease includes an effective component that is a material suppressing an expression of a gene encoding a monoamine oxidase B (MAO-B) in a reactive astrocyte, or a material reducing an activity of an MAO-B protein.

In one embodiment, the material reducing the activity of the MAO-B protein may be a compound selected from the group consisting of a compound represented by Formula 1 below, a pharmaceutically acceptable salt thereof, an isomer thereof, a solvate thereof, a hydrate thereof, and a combination thereof.

Formula I

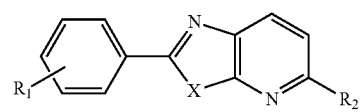

wherein, in Formula 1 above, $R_1$ and $R_2$ are each independently a hydrogen atom, a halogen atom, a nitro group, a cyano group, a carboxyl group, a hydroxyl group, a substituted or unsubstituted $C_1$-$C_{12}$ alkyl group, a substituted or unsubstituted $C_2$-$C_{12}$ alkenyl group, a substituted or unsubstituted $C_2$-$C_{12}$ alkynyl group, a substituted or unsubstituted $C_3$-$C_{15}$ cycloalkyl group, a substituted or unsubstituted $C_3$-$C_{40}$ heterocycloalkyl group, (a substituted or unsubstituted $C_6$-$C_{20}$ aryl) $C_1$-$C_{12}$ alkyl group, a substituted or unsubstituted $C_1$-$C_{12}$ alkoxy group, a substituted or unsubstituted $C_6$-$C_{20}$ arylamine group, a substituted or unsubstituted $C_6$-$C_{30}$ diarylamine group, a substituted or unsubstituted $C_6$-$C_{20}$ aryloxy group, a substituted or unsubstituted $C_6$-$C_{20}$ aryl group, or a substituted or unsubstituted $C_5$-$C_{20}$ heteroaryl group; and X is —O—, —S—, or —N(H)—.

As used herein, the term "alkyl" refers to a monovalent saturated, branched, or straight hydrocarbon group derived by removing one hydrogen atom from a single carbon atom of a parent alkane. Non-limiting examples of the alkyl group are methyl, ethyl, propyl, such as propane-1-yl, propane-2-yl, and cyclopropane-1-yl, and butyl, such as butane-1-yl, butane-2-yl, 2-methyl-propane-1-yl, 2-methyl-propane-2-yl, cyclobutane-1-yl, and tert-butyl. In some other embodiments, the alkyl group may include from 1 to 12 carbon atoms. At least one hydrogen atom in the alkyl group may be substituted with a halogen atom, a hydroxyl group, a lower alkyl group, or the like. The term "lower alkyl" refers to an alkyl group including from 1 to 6 carbon atoms.

The term "alkenyl" refers to an unsaturated branched, straight, or cyclic alkyl group with at least one carbon-carbon double bond derived by removing one hydrogen atom from a single carbon atom of a parent alkene. The alkenyl group may be in Z- or E-form (or a cis or trans form), near the double bond. Non-limiting examples of the alkenyl group are ethenyl; propenyl, such as prop-1-ene-1-yl, prop-1-ene-2-yl, prop-2-ene-1-yl(allyl), prop-2-ene-2-yl, and cycloprop-1-ene-1-yl; cycloprop-2-ene-1-yl; and butenyl, such as but-1-ene-1-yl, but-1-ene-2-yl, 2-methyl-prop-1-ene-1-yl, but-2-ene-1-yl, but-2-ene-2-yl, buta-1,3-diene-1-yl, buta-1,3-diene-2-yl, cyclobut-1-ene-1-yl, cyclobut-1-ene-3-yl, and cyclobuta-1,3-diene-1-yl. In some embodiments, the alkenyl group may include from 2 to 12 carbon atoms, and in some other embodiments, may be a "lower alkenyl" group having from 2 to 6 carbon atoms.

The term "alkynyl" refers to an unsaturated branched or straight hydrocarbon group with at least one carbon-carbon triple bond derived by removing one hydrogen atom from a single carbon atom of a parent alkyne. Non-limiting examples of the alkynyl groups are ethinyl, propynyl, butynyl, 2-pentynyl, 3-pentynyl, 2-hexynyl, and 3-hexynyl. In some embodiments, the alkynyl group may have from 2 to 12 carbon atoms, and in some other embodiments, may be a "lower alkynyl" group having from 2 to 6 carbon atoms.

The term "alkoxy" refers to a radical —OR, wherein R is an alkyl group. Non-limiting examples of the alkoxy group are methoxy, ethoxy, propoxy, butoxy, and cyclohexyloxy.

The term "aryl" refers to a monovalent aromatic hydrocarbon group derived by removing one hydrogen atom from a single carbon atom of a parent aromatic ring system. The aryl group may include a 5- and 5-membered carbocyclic aromatic ring, for example, benzene; a bicyclic system of which at least one ring may be a carbocyclic and aromatic group, such as naphthalene, indane, and tetraline; a tricyclic system of which at least one ring may be a carbocyclic and aromatic group, such as fluorene. For example, the aryl group may include a 5- and 5-membered carbocyclic aromatic ring fused to a 5- to 7-membered heterocycloalkyl group including at least one heteroatom selected from among N, O, and S. In some embodiments the aryl group may include from 6 to 10 carbon atoms. However, the aryl does not include or overlap with heteroaryl groups independently defined below. Therefore, if at least one carbocyclic aromatic ring is fused with a heterocycloalkyl aromatic ring, a resulting cyclic system is a heteroaryl defined herein, not an aryl group.

The term "carboxy" refers to a radical —C(O)OH.

The term "cyano" refers to a radical —CN.

The term "cycloalkyl" refers to a saturated or unsaturated nonaromatic cyclic alkyl group. To define a certain level of saturation, the term "cycloalkaneyl" or "cycloalkenyl" is used. Non-limiting examples of the cycloalkyl are groups derived from cyclopropane, cyclobutane, cyclopentane, and cyclohexane. In some other embodiments, the cycloalkyl group may be a C3-10 cycloalkyl group, for example, a C3-6 cycloalkyl group.

The term "heterocycloalkyl" refers to a saturated or unsaturated non-aromatic cyclic alkyl group, wherein at least one carbon atom (and relevant hydrogen atom) may be independently appropriately substituted with the same or a different heteroatom and a relevant hydrogen atom thereof. Non-limiting examples of the heteroatoms are N, P, O, S, and Si. Non-limiting examples of the heterocycloalkyl group are groups derived from epoxide, imidazolidine, morpholine, piperazine, piperidine, pyrazolidine, pyrrolidine, quinuclidine, tetrahydrofuran, tetrahydropyran, or the like. Examples of the substituted heterocycloalkyl are cyclic systems substituted with at least one oxo(=O) or oxide (—O—) group, such as piperidineyl N-oxide, morpholinyl-N-oxide, 1-oxo-1-thiomorpholinyl, and 1,1-dioxo-1-thiomorpholinyl.

The term "halo" refers to a fluoro group, a chloro group, a bromo group, or an iodo group.

The term "heteroaryl" refers to a monovalent heteroaromatic group derived by removing one hydrogen atom from a single atom of a parent heteroaromatic ring system. The heteroaryl group may include a 5- to 7-membered aromatic, monocyclic ring including at least one heteroatom, for example, 1 to 4 heteroatoms, and in some embodiments, 1 to 3 heteroatoms, selected from among N, O, and S, and carbon atom in the rest of the rings; a polycyclic heterocycloalkyl ring including at least one heteroatom, for example, 1 to 4 heteroatoms, and in some embodiments, 1 to 3 heteroatoms, selected from among N, O, and S, and carbon atom in the rest of the rings; and a polycyclic heterocycloalkyl ring including at least one heteroatom in an aromatic ring. In some embodiments, the heteroaryl group may include a 5- to 7-membered heteroaromatic ring fused with a 5- to 7-membered cycloalkyl ring; and a 5- to 7-membered heteroaromatic ring fused with a 5- to 7-membered heterocycloalkyl ring. In these fused bicyclic heteroaryl rings in which only one ring contains at least one heteroatom, the heteroaromatic ring or cycloalkyl ring may be a fusing site. If a total number of S and O atoms in the heteroaryl group is greater than 1, the heteroatoms may not be adjacent to each other. In some embodiments, the total number of S and O atoms in the heteroaryl group may be 2 or less, and in some other embodiments, may be 1 or less. The heteroaryl group does not include or overlap with the aryl groups as defined above. Non-limiting examples of the heteroaryl group are groups derived from acridine, arsindole, carbazole, β-carboline, chromane, chromene, cinnoline, furan, imidazole, indazole, indole, indulines, idolizing, isobenzofuran, isochromene, isoindole, isoindoline, isoquinoline, isothiazole, isoxazole, naphthyridine, oxadiazole, oxazole, perinidine, phenanthridine, phenanthroline, phenazine, phthalazine, pterdine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthenes, or the like. In some embodiments, the heteroaryl group may be a 5- to 20-membered heteroaryl group, for example, a 5- to 10-membered heteroaryl group. Non-limiting examples of the heteroaryl group are groups derived from thiophene, pyrrole, benzothiophene, benzofuran, indole, pyridine, quinoline, imidazole, oxazole, and pyrazine.

In some embodiments, in the compound of Formula 1 above, $R_1$ and $R_2$ may be each independently a hydrogen atom, a halogen atom, a nitro group, a cyano group, a substituted or unsubstituted $C_1$-$C_{12}$ alkyl group, or a substituted or unsubstituted $C_1$-$C_{12}$ alkoxy group, wherein X may be —O—, or —S—.

In some embodiments, the material reducing the activity of the MAO-B protein may be N-cyclohexyl-2-phenyloxazolo[5,4-b]pyridine, 2-phenyl-5-(pyrrolidine-1-yl)oxazolo[5,4-b]pyridine, 2-phenyl-5-(pyrrolidine-1-yl)thiazolo[5,4-b]pyridine, 2-(2-chlorophenyl)-5-(pyrrolidine-1-yl)oxazolo[5,4-b]pyridine, 2-(3-chlorophenyl)-5-(pyrrolidine-1-yl) oxazolo[5,4-b]pyridine, 2-(4-fluorophenyl)-5-(pyrrolidine-1-yl)oxazolo[5,4-b]pyridine, 2-phenyl-5-(piperidine-1-yl) oxazolo[5,4-b]pyridine, 2-phenyl-5-(piperidine-1-yl) thiazolo[5,4-b]pyridine, 2-(2-chlorophenyl)-5-(piperidine-1-yl)oxazolo[5,4-b]pyridine, 2-(3-fluorophenyl)-5-(piperidine-1-yl)oxazolo[5,4-b]pyridine, 2-(3-chlorophenyl)-5-(piperidine-1-yl)oxazolo[5,4-b]pyridine, 3-(5-(piperidine-1-yl)oxazolo[5,4-b]pyridine-2-yl)benzonitrile, 2-(4-fluorophenyl)-5-(piperidine-1-yl)oxazolo[5,4-b] pyridine, 2-(4-bromophenyl)-5-(piperidine-1-yl)oxazolo[5,4-b]pyridine, 2-(4-methoxyphenyl)-5-(piperidine-1-yl) oxazolo[5,4-b]pyridine, 2-(3-chlorophenyl)-N-methyloxazolo[5,4-b]pyridine-5-amine, or 2-(4-chlorophenyl)-N-methyloxazolo[5,4-b]pyridine-5-amine.

According to another aspect of the present disclosure, a pharmaceutical composition for preventing or treating a degenerative brain disease includes an effective component that is a material changing a subcellular localization pattern of bestrophine 1 channel in a reactive astrocyte from a cell body and a main process into a microdomain direction.

According to another aspect of the present disclosure, a pharmaceutical composition for preventing or treating a degenerative brain disease includes an effective component that is a material inducing an expression of a gene encoding a GABA transaminase in a reactive astrocyte, or a material increasing an activity of a GABA transaminase protein.

In some embodiments, the pharmaceutical composition may include nucleotides, antisense, shRNA, siRNA oligonucleotides, or natural extracts as an effective component.

In some embodiments, the degenerative brain disease may be selected from the group consisting of Alzheimer's disease, mild cognitive impairment, vascular dementia, frontotemporal dementia, Louis corpuscle dementia, Creutzfeld-Jakob disease, traumatic head injuries, syphilis, acquired immune deficiency syndrome (AIDS), viral infection, brain abscess, brain tumor, sclerosis, dementia in metabolic disease, hypoxia, Parkinson's disease, Huntington's disease, Pick's disease, amyotrophic lateral sclerosis (ALS), epilepsy, ischemia, stroke, attention deficit hyperactivity disorder (ADHD), schizophrenia, depression, manic-depression, stress disorder, spinal cord injury, and myelitis, but are not limited thereto.

The pharmaceutical composition may include a pharmaceutically acceptable carrier. Non-limiting examples of the pharmaceutically acceptable carrier that may be used in the pharmaceutical field include commonly-used lactose, dextrose, sucrose, sorbitol, mannitol, starch, gum acacia, calcium phosphate, alginates, gelatin, calcium silicate, microcrystalline cellulose, polyvinylpyrrolidone, cellulose, water, syrup, methyl cellulose, methyl hydroxy benzoate, propyl hydroxy benzoate, talc, magnesium stearate, and mineral oil, but is not limited thereto. The pharmaceutical composition may further include, for example, a lubricant, a wetting agent, a sweetener, a flavor enhancer, an emulsifying agent, a suspending agent, a preservative, or the like. Other suitable pharmaceutically acceptable carriers and drugs are described in *Remington's Pharmaceutical Sciences* (19th ed., 1995). The pharmaceutical composition may be orally or parenterally administered (for example, via intravenous injection, intraperitoneal injection, intramuscular injection, subcutaneous injection, or local administration)

A suitable dosage of the pharmaceutical composition may depend on a variety of factors, including formulation methods, administration methods, ages of patients, body weight, gender, pathologic conditions, diet, administration time, administration route, excretion speed, and reaction sensitivity. In some embodiments, a dosage of the pharmaceutical composition may be from about 0.001 to about 100 mg/kg (of body weight) a day.

The pharmaceutical composition may be formulated with a pharmaceutically acceptable carrier and/or an excipient in the form of a unit or multiple dosage(s) by a well-known method in the art. In this regard, the formulation may be a solution in oil or an aqueous medium, a suspension, an emulsified solution, an extract, powder, granules, a tablet, or a capsule, and may further include a dispersing or a stabilizing agent.

One or more embodiments of the present disclosure will now be described in detail with reference to the following examples. However, these examples are for illustrative purposes only and are not intended to limit the scope of the one or more embodiments of the present disclosure.

Example 1-1

Verification of Increased GABA in Reactive Astrocytes of a Mouse Model with Alzheimer's Disease To identify whether an amount of GABA was increased in reactive astrocytes changed from normal astrocytes by Alzheimer's disease, an immunohistochemical analysis of a well-known APPswe/PSEN1 transgenic mouse model of Alzheimer's disease (purchased from The Jackson Laboratory, http://www.jax.org) was performed. After immunostaining a sample tissue, further staining with thioflavin-S was performed to observe amyloid plaque as a feature of Alzheimer's disease. After deeply anesthetizing an about 8- to 9-month aged APPswe/PSEN1 mouse with Avertin, perfusion fixation was followed using 4% paraformaldehyde. After isolating the brain from the mouse, a coronal cryostat section having a thickness of about 30 μm from the hippocampus was washed with phosphate buffered saline (PBS) three times, and was then reacted with a blocking solution (0.3% Triton-X, 2% normal serum in 0.1M PBS, available from Sigma) for about 1 hour. The resultant was shaking-cultured together with Chicken anti-GFAP antibody (1:500, Chemicon) and guinea pig anti-GABA antibody (1:1000, available from Chemicon) at 4° C. overnight. The resulting cultured product was washed with PBS three times, was subsequently reacted with anti-chicken Alexa 488 (1:200, Invitrogen) and anti-guinea pig Alexa 647 (1:200, Invitrogen) that were conjugated with corresponding secondary antibodies, for about 3 hours, and then was washed again with PBS three times. A resulting product was reacted with a solution of 1 mM thioflavin-S dissolved in an aqueous solution of 50% ethanol for about 8 minutes, and then was washed twice with 80% ethanol each for 10 seconds, and then three times with tertiary distilled water each for 10 seconds.

The tissue stained was moved into PBS and then onto a slide glass, and then mounted onto a mounting medium (Dako) to be observed using an FV1000 confocal microscope (Olympus) to obtain a series of confocal fluorescence images, which were then processed with Olympus FLUOVIEW software ver. 2.1.

High-magnification (×40) confocal immunohistochemical images of the resulting hippocampus of the transgenic APPswe/PSEN1 mouse were obtained using antibodies against GFAP and GABA. The results are shown in FIG. 1. Referring to FIG. 1, amyloid plaques (blue), which are not found in normal mice, were observed in the hippocampus of the mouse model of Alzheimer's disease. Reactive astrocytes (green) in the Alzheimer's disease model were found to be stained in astrocyte marker GFAP (green) and to have increased cell body size and increased thickness of the main process, as compared with normal astrocytes. Zero or almost zero GABA (red) appeared in the normal astrocytes, while the amount of intracellular GABA was dramatically increased. With regard to interneurons stained with anti-GABA antibody, but not stained with anti-GFAP antibody, there was found no difference in size or degree of GABA staining between the normal mouse and the Alzheimer mouse model.

Example 1-2

Figure 9:
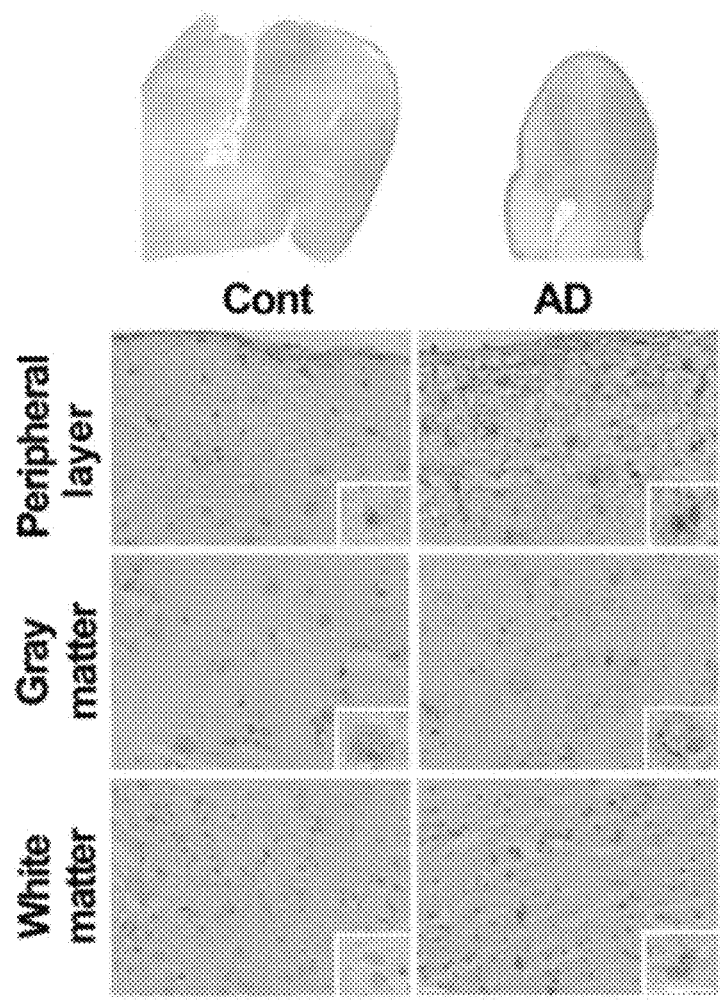
FIG. 9 shows microscopic images illustrating GABA reactive astrocytes of postmortem cerebral tissues from a human Alzheimer patient and a normal subject.

Verification of Increased GABA in Alzheimer Patient's Cerebral Reactive Astrocytes To identify whether an amount of GABA was increased in Alzheimer patient's reactive astrocytes with a change of normal astrocytes into the reactive astrocytes, an immunohistochemical analysis was performed using postmortem cerebral tissues (from School of Medicine in Boston University) from a normal subject and an Alzheimer patient. 30 μm-thick coronal cryostat sections were obtained from the fixed postmortem brain tissues, and were then reacted in a hydrogen peroxide solution to suppress activity of the peroxidase remaining in the tissue, followed by washing them with PBS three times, and reacting them in a blocking solution (0.3% Triton-X, 2% normal serum in 0.1M PBS, available from Sigma) for about 1 hour. Next, a mixture of the sample tissues with a guinea pig anti-GABA antibody (1:1000, Chemicon) was incubated while shaking at about 4° C. overnight. The resulting product was washed with PBS three times, and was then reacted with a corresponding secondary antibody-conjugated anti-guinea pig horseradish peroxidase (HRP) (1:200, Invitrogen) for about 3 hours, followed by washing with PBS three times. Next, the resulting product was reacted with a DAB solution until it was stained brown by the activity of the HRP, and was then transferred into PBS, mounted onto a slide glass, and then onto a mounting medium (available from Dako) for optical microscopic observation. High-magnification (×40) immunohistochemical images of the postmortem cerebral tissues from the normal subject and the Alzheimer patient were obtained. The results are shown in FIG. 9. Referring to FIG. 9, no or nearly no GABA (brown color) was not found in the cerebral astrocytes from the normal subject, and a sharp increase in the amount of subcellular GABA was found in the Alzheimer patient's cerebral astrocytes. These results indicate that GABA-accumulating reactive astrcytes are found both in the Alzheimer mouse model and human patients, and thus supporting that the present disclosure may be applicable in preventing or treating Alzheimer disease.

Example 2-1

Verification of Expression Changes in MAO-B, Bestrophine 1 and GABA Transaminase in Reactive Astrocytes To investigate changes in MAO-B, bestrophine 1, and GABA transaminase in reactive astrocytes, immunohistochemical staining was performed in the same manner as in Example 1, except that different types of antibodies were added.

Figure 2:
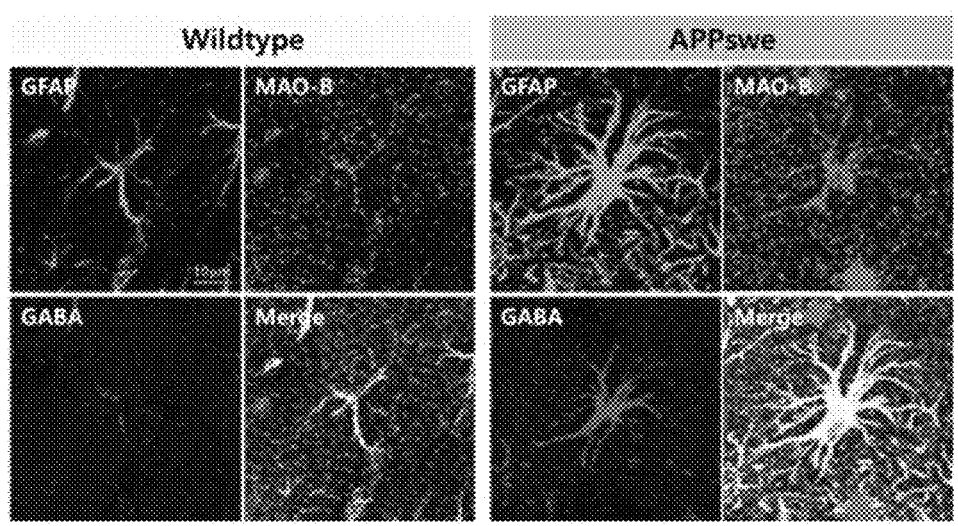
FIG. 2 shows confocal fluorescent images illustrating an amount of expression of monoamine oxidase B (MAO-B) in the hippocampal reactive astrocytes of the mouse model of Alzheimer's disease.
Figure 3:
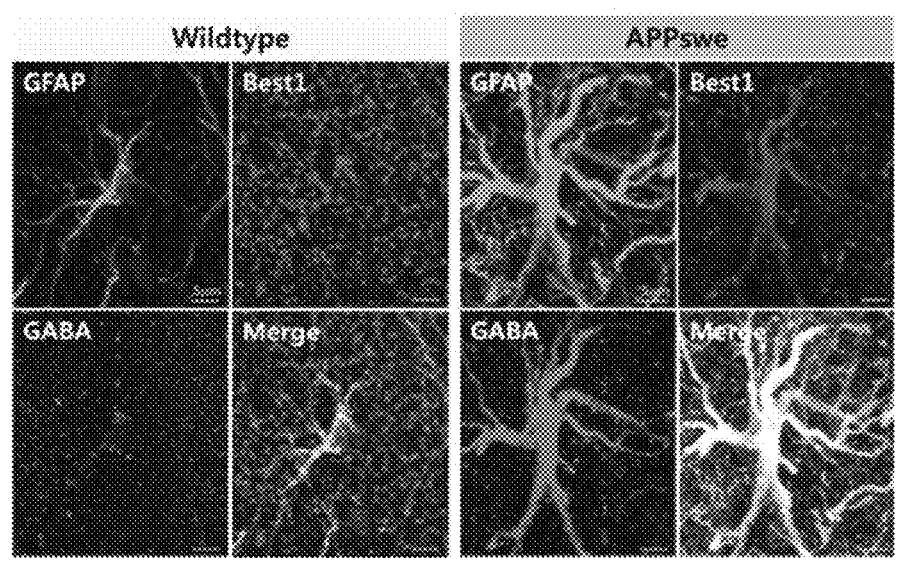
FIG. 3 shows confocal fluorescent images illustrating a subcellular localization pattern of bestrophine 1 channel in the hippocampal reactive astrocytes of the mouse model of Alzheimer's disease.
Figure 4:
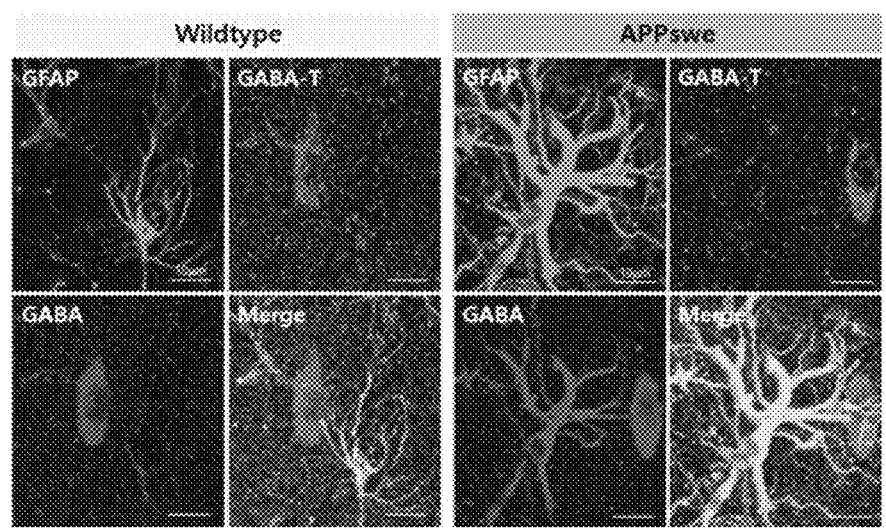
FIG. 4 shows confocal fluorescent images illustrating an amount of expression of GABA transaminase in the hippocampal reactive astrocytes of the mouse model of Alzheimer's disease.

As primary antibodies, further to the chicken anti-GFAP antibody (1:500, Chemicon) and guinea pig anti-GABA antibody (1:1000, Chemicon), a rabbit anti-MAO-B antibody (1:50, Sigma), rabbit anti-Best 1 antibody (1:100, Soria et al. 2006), or a rabbit anti-GABA transaminases antibody (1:100 Epitomics) was added. As secondary antibodies, further to the anti-chicken DyLight 488 (1:200, Jackson IR) and anti-guinea pig Alexa 647 (1:200, Invitrogen), an anti-rabbit Alexa 555 (1:200 Invitrogen) was added for reaction As a result, as seen in FIG. 2, an increase in MAO-B was found in the reactive astrocytes, and referring to FIG. 3, a reduced expression of the GABA transaminase was found in the reactive astrocytes. The increased expression of the MAO-B and the reduced expression of the GABA transaminase lead to increased GABA in the reactive astrocytes. Referring to FIG. 4, as compared with the wild type, a change in subcellular localization of bestrophine 1 was found in the reactive astrocytes, indicating that a changed secretion pattern of GABA resulting from the changed subcellular localization of bestrophine 1 leads to Alzheimer's disease.

Example 2-2

Verification of Increased Cerebral MAO-B Protein Activity in Alzheimer Mouse Model A stock solution was prepared using a human MAO-B enzyme (purchased from Aldrich) and a Amplex® Red monoamine oxidase assay kit according to a preparation manual. The kit includes a 5× reaction buffer, an Amplex® red reagent (1 mg), HRP (horseradish peroxidase), DMSO, $H_2O_2$, p-tyramine (substrate of MAO-A, B), benzylamine (substrate of MAO-B), clorgiline (inhibitor of MAO-A), and pargyline (inhibitor of MAO-B). Among these reagents in the kit, benzylamine was used as a substrate for MAO-B, and pargyline was used as an MAO-B inhibitor. A solution as overall substrates was prepared as follows.

200 ul of a solution of 1 mg of Amplex® red sufficiently dissolved in 200 ul of DMSO, 100 ul of a mixed solution of HRP and 1 ml of a 1× buffer, 200 ul of a solution of benzylamine dissolved in 1.2 ml of $dH_2O$ were added to 9.5 ml of a 1× buffer to reach a total volume of 10 mL, which is sufficient for 100 wells. 0.5 ul of a mixture of MAO-B inhibitor pargyline and 1 ml of $dH_2O$ was put into each well.

First, a hippocampal extract from the Alzheimer mouse was put into $1^{st}$ and $2^{nd}$ rows of the 96 wells, while a hippocampal extract from the normal mouse was put into $3^{rd}$ and $4^{th}$ rows of the wells. After anesthetizing the mice, the hippocampus was isolated from each mouse, followed by separating a CA1 region and a DG region from the hippocampus. Immediately after being separated from the hippocampus, the fresh tissues from each mouse were homogenized in a homogenization solution. A relatively large tissue lump was removed by weak centrifugation, and a supernatant was collected and centrifuged at a high speed (13000 rpm for 20 minutes) to obtain a mitocondria-rich precipitate. The precipitate obtained from the hippocampus was used by about 50 micrograms per each well to determine the activity of the MAO-B enzyme. 0.5 ul of a pargyline, the MAO-B inhibitor was further added into the $2^{nd}$ and $4^{th}$ row of the wells. To reduce an experimental error for accuracy, the test was repeated three times for each compound. After 30 minutes, 100 ul of the substrate solution was added into each well in a darkroom. The test was performed in the darkroom due to light sensitivity of the Amplex® reagent. Finally, a total volume of the reaction solution per well reached 200 ul. After about 2 to 3 hours, chromophoric degrees of the samples were measured. A variation in data values for the $1^{st}$ and $2^{nd}$ rows of the wells indicates the pure reaction activity of the MAO-B enzyme with the substrate in the hippocampus of the Alzheimer mouse. A variation in data values for the $3^{rd}$ and $4^{th}$ rows of the wells indicates the pure reaction activity of the MAO-B enzyme with the substrate in the hippocampus of the normal mouse.

Figure 14:
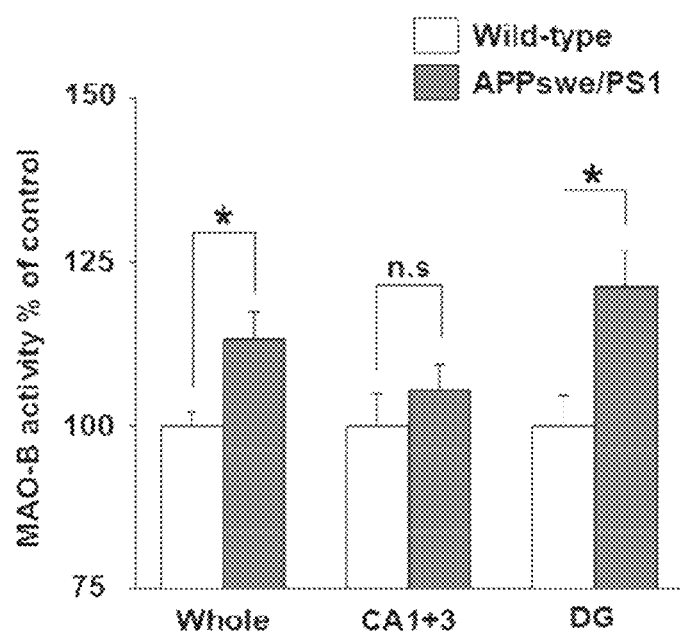
FIG. 14 is a graph illustrating activity of an MAO-B enzyme in a hippocampal extract of an Alzheimer model mouse.

Referring to FIG. 14, the Alzheimer mouse was found to have a higher hippocampal MAO-B activity in the hippocampal extract as compared with the normal mouse, and in particular, in the hippocampal DG region by about 25%, indicating that an increased MAO-B activity causes Alzheimer's disease.

Example 2-3

Verification of Increased MAO-B Expression in Alzheimer Patient's Cerebral Reactive Astrocytes To investigate changes in expression of MAO-B in reactive astrocytes, immunohistochemical staining was performed using postmortem cerebral tissues of the Alzheimer patient in the same manner as in Example 2, except that additional types of antibodies were used.

A chicken anti-GFAP antibody (1:500, Chemmicon), guinea pig anti-GABA antibody (1:1000, Chemicon), and rabbit anti-MAO-B antibody (1:50, Sigma) were used as primary antibodies. As secondary antibodies, further to the anti-chicken DyLight 488 (1:200, Jackson IR) and anti-guinea pig Alexa 647 (1:200, Invitrogen), an anti-rabbit Alexa 555 (1:200 Invitrogen) was added for reaction.

As a result, as shown in FIG. 10A, the expression of the MAO-B was found to be increased in the reactive astrocytes. This increased expression of the MAO-B led to an increased in GABA in the reactive astrocytes. This indicates that an increased expression of MAO-B in human reactive astrocytes of the Alzheimer patient causes an increase in GABA and consequently Alzheimer disease.

An increased expression level of cerebral MAO-B mRNA in the Alzheimer patient was identified using quantitative RT-PCR. Total RNA was prepared from the postmortem cerebral tissues of the Alzheimer patient. First-strand cDNA was prepared from the total RNA using an oligo (dT) primer and a reverse transferase. Subsequently, PCR was performed using the first-strand cDNA as a template and a gene-specific primer set encoding a MAO-B protein and a GFAP protein. The resulting amplified PCR product was subjected to electrophoresis, and subsequently the resulting bands were analyzed to measure changes in expression of the genes encoding the proteins were measured by band analysis.

Figure 10:
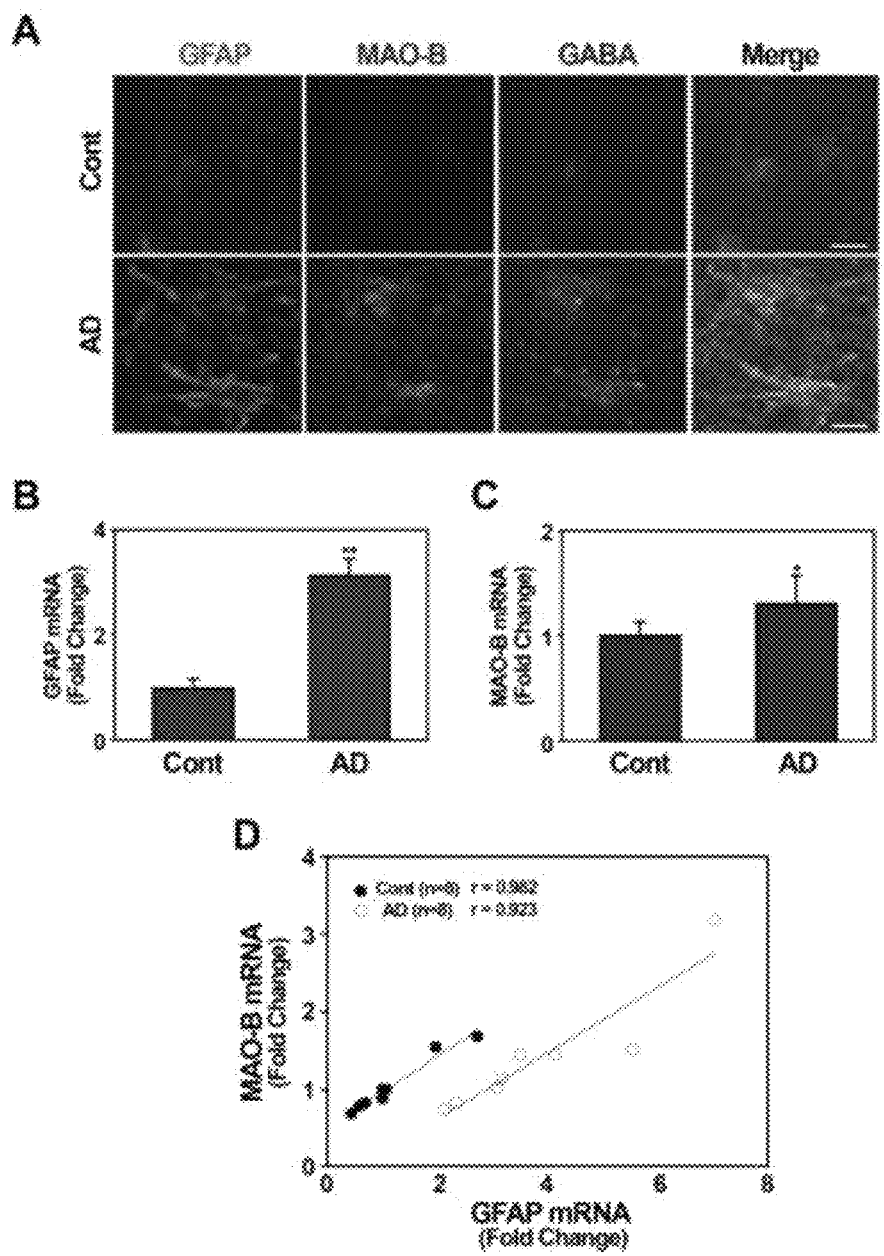
FIG. 10 shows confocal fluorescent images illustrating expression levels of MAO-B and GABA in the reactive astrocytes of the postmortem cerebral tissues from the human Alzheimer patient, and a plot of correlation between expression levels of GFAP and MAO-B.

As a result, an expression level of GFAP as an astrocyte marker in the Alzheimer patient's brain was increased as shown in FIG. 10B, and an increased expression level of the MAO-B enzyme producing GABA was also found as shown in FIG. 10. FIG. 10D is a plot of correlation between the expression levels of GFAP and MAO-B in each patient sample. This indicates that expression levels of both MAO-B protein and MAO-B mRNA were increased in the Alzheimer patient's brain.

Example 3-1

Figure 5:
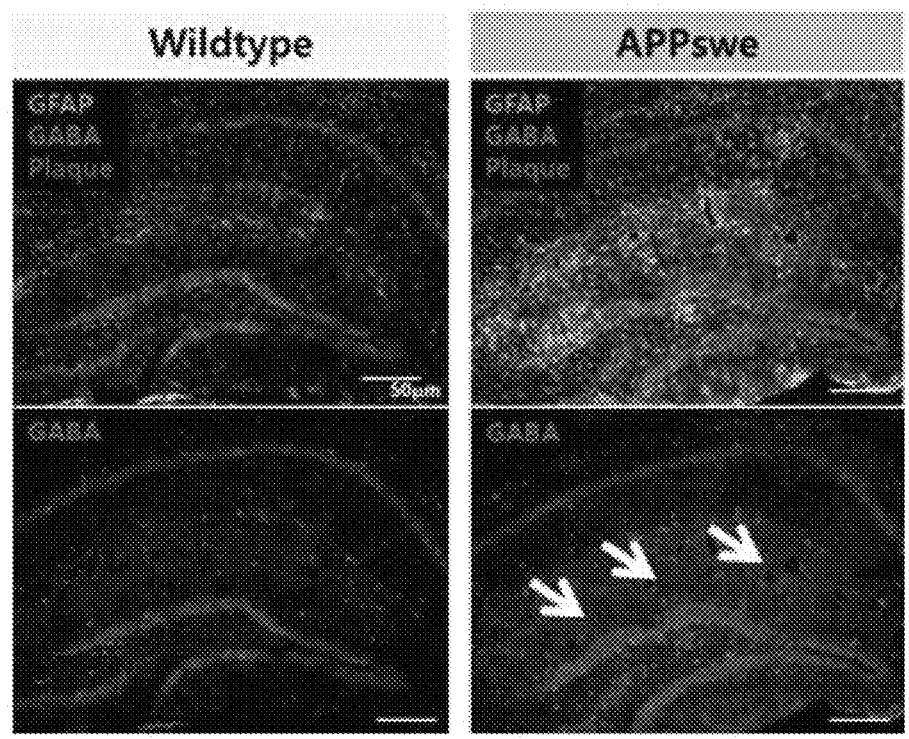
FIG. 5 shows confocal fluorescent images illustrating distribution of GABA in the hippocampal tissue of the mouse model of Alzheimer's disease.

Verification of Increase in Hippocampal Tonic GABA from Production of GABA in Reactive Astrocytes of Alzheimer Mouse Model Low-magnification (×10) confocal fluorescent images were obtained from the slide sample manufactured in Example 1 using an FV1000 confocal microscope (Olympus). As seen in FIG. 5, a GABA-stained area was increased in most of the hippocampal dentate gyrus molecular layer of the Alzheimer mouse model (denoted by white arrows), meaning that the amount of GABA was increased both in and outside the cells. As in Example 2, an increased expression of MAO-B in the reactive astrocytes led to subcellular accumulation of GABA, and a change in subcellular localization of bestrophine 1 led to exocytic secretion of GABA to become tonic GABA. This change in secretional pattern of the GABA is considered to cause Alzheimer's disease.

Example 3-2

Verification of Increased Hippocampal Extracellular GABA Resulting from GABA Production in Reactive Astrocytes of Alzheimer Model Mouse An increased level of hippocampal extracellular GABA in the Alzheimer model mouse was identified using microdialysis and high-performance liquid chromatography (HPLC). After being anesthetized with isoflurane, the Alzheimer model mouse was fixed in a stereotaxic instrument, and a guide cannula and a microdialysis probe was implanted into an amyloid plaque-rich region of the hippocampus, as shown in FIGS. 15a and 15b. After completely waking up from the anesthesia, an artificial cerebrospinal fluid (ASCF) was flowed through the probe during microdialysis, and then liquid from the microdialysis was collected at 20-minute intervals and was then analyzed using HPLC to measure a GABA level in each liquid sample.

Figure 15:
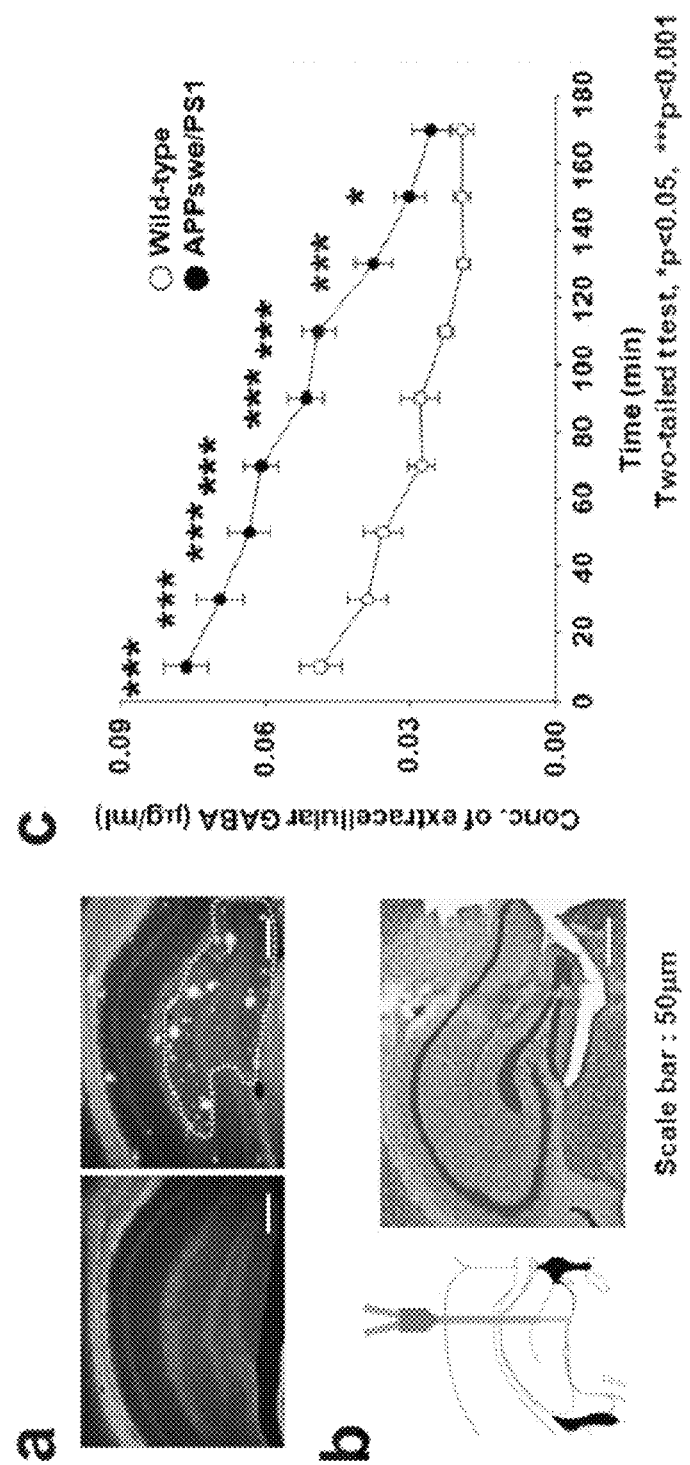
FIG. 15 is a figure and a graph illustrating concentration of GABA in hippocampal tissues of the Alzheimer model mouse.

Referring to FIG. 15, the Alzheimer model mouse was found to be higher in hippocampal extracellular GABA level by about 2 times, as compared with the normal mouse. This indicates that GABA produced and accumulated in the reactive astrocytes was released out of the cells, becoming tonic GABA, and the increased release of GABA led to Alzheimer disease.

Example 3-3

Verification of Increased Hippocampal Neuro-Inhibitory Signal Resulting from GABA Production in Reactive Astrocytes of Alzheimer Model Mouse The degree in which the hippocampal neurons of the Alzheimer model mouse were affected by a GABA-mediated inhibitory signal was measured using whole-cell patch clamp recording.

After being anesthetized with halothane, the Alzheimer model mouse was decapitated, followed by quick extraction of the brain from the skull, and soaking it in an ice-cold cutting solution including: 250 mM sucrose, 26 mM $NaHCO_3$, 10 mM D(+)-glucose, 4 mM $MgCl_2$, 3 mM myo-inositol, 2.5 mM KCl, 2 mM Sodium pyruvate, 1.25 mM $NaH_2PO_4$, 0.5 mM Ascorbic acid, 0.1 mM $CaCl_2$, and 1 mM Kynurenic acid (pH 7.4). All solutions were gas-treated with 95% $O_2$-5% $CO_2$. After trimming the forehead and cerebellum parts using a knife, and 300-micrometer-thick slices containing the hippocampus were cut using a microtome (Leica VT 1000), and transferred to artificial cerebrospinal fluid (ASCF) solution including; 126 mM NaCl, 24 mM $NaHCO_3$, 1 mM $NaH_2PO_4$, 2.5 mM KCl, 2.5 mM $CaCl_2$, 2 mM $MgCl_2$, and 10 mM D(+)-Glucose (pH 7.4). Slices were incubated for about 40 minutes at least at room temperature. For whole-cell patch clamp recording, hippocampal slices were transferred to an electrophysiological recording chamber (RC-26G, Warner Instruments) which is continuously superfused with artificial cerebrospinal fluid (ASCF) solution (flow rate; 2 ml/min) and controlled by a flow controller (Synaptosoft) and a vacuum pump (Charles Austen, model Capex 8C). Slice chamber was mounted on the stage of an upright microscope (Olympus, Japan) and viewed with an X60 water immersion objective with differential interference contrast and infrared optics. Cellular morphologies were visually identified by Imaging Workbench 6.0 (INDEC Systems, Inc), camera controller (Hamamatsu, C4742-95), and light microscope controller (Olympus, TH4-200). Whole cell voltage-clamp recording was made from granular cell stomas mostly located in the hippocampal dentate gyrus.

For granular cell recording patch pipettes (8-12 MΩ) were constructed from thick-walled borosilicate glass capillaries (SC150E-10, Warner instrument Corp), and pipette was filled with an internal solution containing; 135 mM CsCl, 4 mM NaCl, 0.5 mM $CaCl_2$, 10 mM HEPES, 5 mM EGTA, 2 mM Mg-ATP, 0.5 mM $Na_2$-GTP, and 10 mM QX-314 (pH adjusted to 7.2 with CsOH) (278-285 mOsmol) (Rossi, et al., 2003). With this internal solution, $E_{cl}=0$ mV with voltage clamp and holding potential of −70 mV, inward current was elicited. During whole-cell patch clamp recording using patch pipettes with granular cells, an artificial cerebrospinal fluid (ASCF) solution containing AP-5 and CNQX was flowed for 5 minutes or longer to suppress neurotransmission facilitated by excitatory neurotransmitter stimulator, and record selectively only a neurosignal induced by the inhibitory material GABA. After 5 minutes, an artificial cerebrospinal fluid (ASCF) solution containing bicuculline that inhibits GABAergic neurotransmission was flowed for about 3 minutes to suppress GABA signals. The amplitude of a tonic GABA signal transferred to the granular cells may be understood by comparing baselines before and after the inhibition with bicuculilline.

The signals were digitized and sampled at 50 μs intervals with Digidata 1440A (Molecular Devices) and Multiclamp 700B amplifier (Molecular Devices) using pCLAMP 10.2 software (Molecular Devices). Off-line analysis was carried out using Clampfit 10.2 (Molecular Devices), SigmaPlot 10.0 (SPSS), and Excel 2003 (Microsoft).

All the drugs and chemicals used in this example were purchased from SIGMA-Aldrich if not mentioned otherwise; QX-314 (Tocris), AP-5 (Tocris), CNQX (Tocris), and bicuculline methobromide (Tocris).

Numerical data was presented as means±S.E.M. The significance of data for comparison was assessed by Student's two-tailed unpaired t test, and significance level was represented as *($p<0.05$), ($p<0.01$), *($p<0.001$). Data was filtered at 2 kHz.

Figure 16:
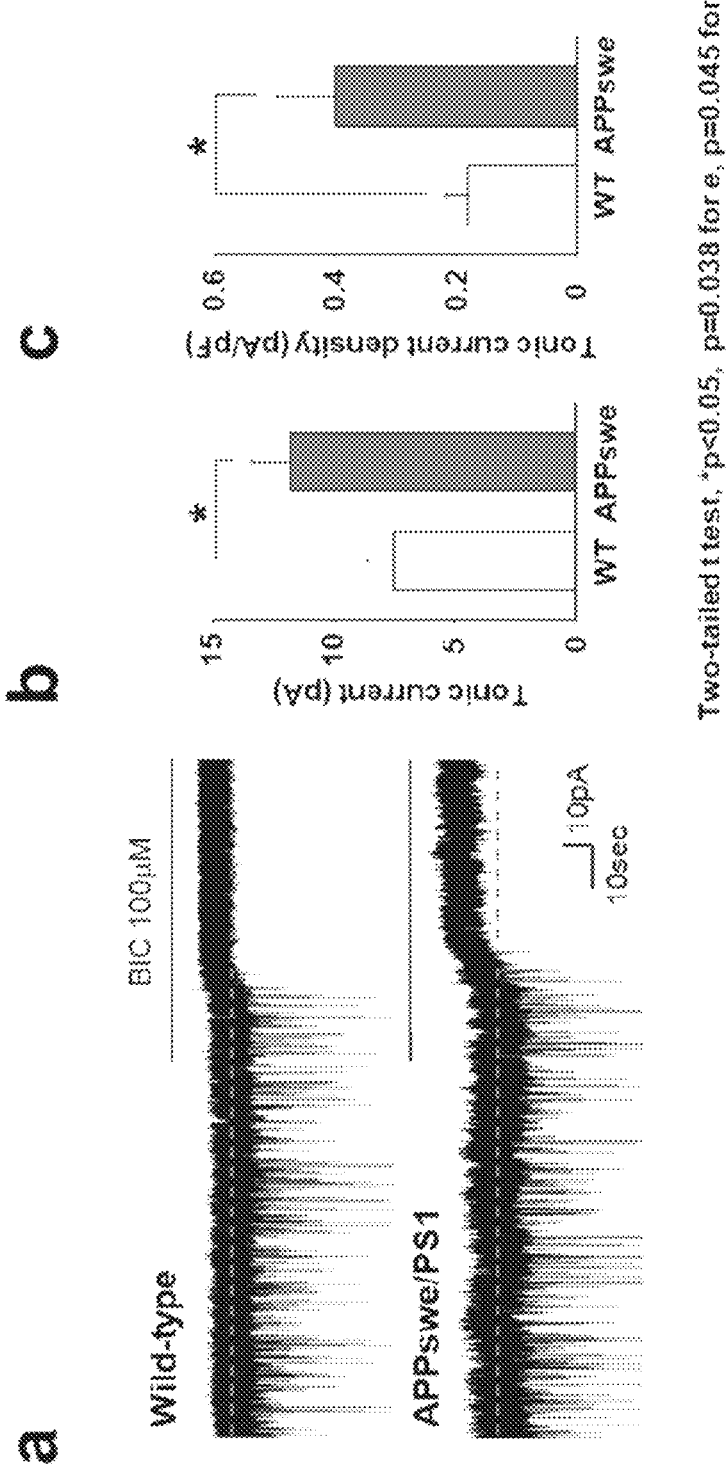
FIG. 16 is a figure and a graph showing inhibitory current levels affected by tonic GABA in hippocampal dentate gyrus granular cells of the Alzheimer model mouse.

As a result, the hippocampal granular cells in the dentate gyrus of the Alzheimer model mouse were found to be more influenced by tonic GABAergic inhibition as compared with the normal mouse (FIG. 16). A current level representing the intracellular influx of chloride ions (Cl—) induced by GABA was about 12 pA for the Alzheimer model mouse and about 8 pA in the normal mouse, both on average. Tonic current density based on the cell area was also higher in the Alzheimer mouse twice then the normal mouse. This indicates that the extracellular efflux of GABA generated in the hippocampal reactive astrocytes of the Alzheimer mouse may inhibit nerve cells. Finally, this may inhibit smooth signal transfer between neurons, impairing normal brain functions, which leads to memory impairment as a main symptom from the Alzheimer disease.

Example 4-1

Verification of Increased GABA in Reactive Astrocytes of Virus-Infected Model Mouse A wildtype C57BL/6 mouse (purchased from The Jackson Laboratory), instead of the Alzheimer model mouse, was used. The wildtype C57BL/6 mouse under anesthesia was fixed to a stereotaxic instrument, and adenovirus expressing a fluorescent FGP protein was injected into a thalamic nuclei domain to induce viral infection. An immunochemical test was performed on the virus-infected mouse in the same manner as in Example 1.

Figure 11:
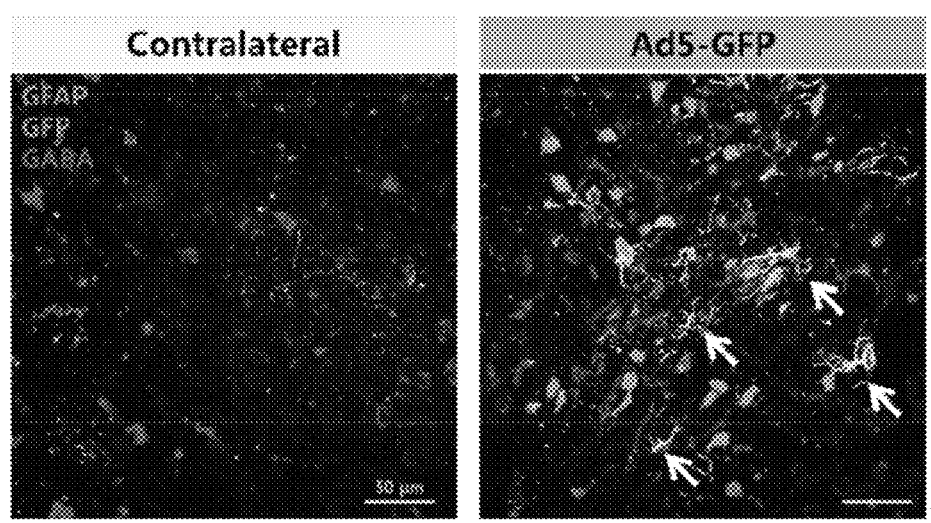
FIG. 11 shows confocal fluorescent images illustrating reactive astrocytes and GABA in reactive astrocytes in the thalamic nuclei domains of a virus-infected model mouse.

Referring to FIG. 11, nearly no GABA was in the astrocytes (green) of the normal thalamic nuclei with no viral infection, whereas GABA-rich astrocytes (yellow) were found in the adenovirus-infected thalamic nucleic as in the Alzheimer model mouse.

These results indicate that GABA-accumulating reactive astrocytes may be generated in Alzheimer disease and other degenerative brain diseases, including viral infection and brain impairment.

Example 4-2

Verification of Increased GABA and Expression Changes of MAO-B and Bestrophine 1 in Reactive Astrocytes in Rat and Mouse Models with Parkinson's Disease A wildtype rat with intracerebrally injected 6-OHDA and a wildtype C57BL/6 mouse with intraperitoneally injected MPTP (purchased from The Jackson Laboratory) were used as Parkinson's disease model rat and mouse, respectively. Dopamine neurons in the substantia nigra pars compacta of the two models were killed to induce Parkinson's symptoms, followed by an immunochemical test in the same manner in Example 1.

Figure 12:
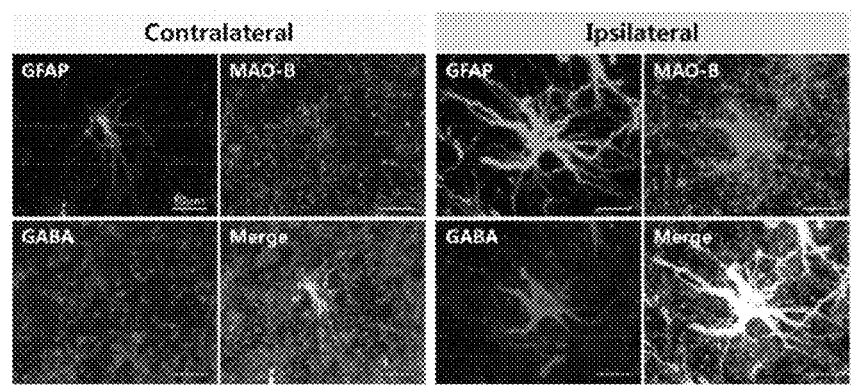
FIG. 12 shows confocal fluorescent images illustrating reactive astrocytes and MAO-B and GABA in the reactive astrocytes in the substantia nigra pars compacta of a Parkinson's model rat.
Figure 13:
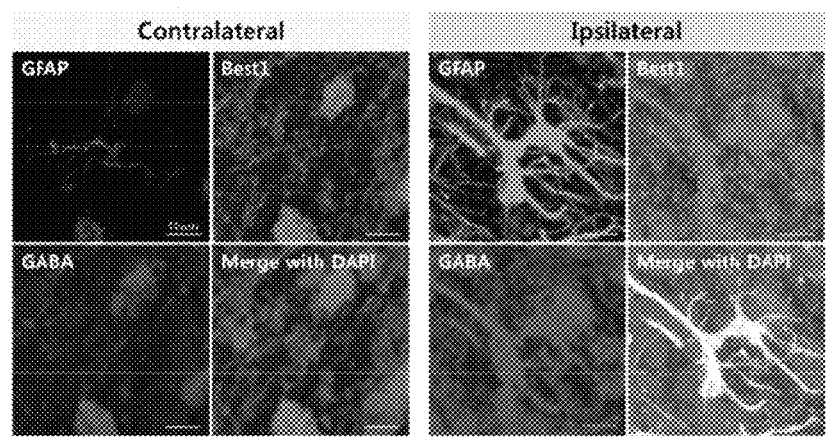
FIG. 13 shows confocal fluorescent images illustrating reactive astrocytes and Best 1 and GABA in the reactive astrocytes in substantia nigra pars compacta of a Parkinson's model mouse.

Referring to FIG. 12, expression levels of both MAO-B and GABA were found to be increased in the Parkinson's model rat, as in the Alzheimer model described above. As shown in FIG. 13, a gradual shift in subcellular localization pattern of bestrophine 1 channel in the reactive astrocytes from a microdomain direction into a cell body and a main process, and an increased expression level of the bestrophine 1 channel were identified in the Parkinson's model mouse. The amount of GABA was also increased in the reactive astrocytes.

These results indicate that GABA-accumulating reactive astrocytes may be generated in Alzheimer disease and other degenerative brain diseases, including Parkinson's disease and brain impairment.

Example 4-3

Verification of Increased GABA and Expression Changes of MAO-B, Bestrophine 1, and GABA Transaminase in Hippocampal Reactive Astrocytes of a Mouse Model with a Hippocampal Injury A transgenic GFAP-EGFP mouse (available from The Jackson Laboratory), instead of the Alzheimer mouse model, was used, in which after anesthetization in the same manner as in Example 1, hippocampal damage was induced by inserting a sharp pin into the hippocampus of the anesthetized mouse. An immunohistochemical test was performed on the mouse on the 5th and 14th days after the hippocampal damage.

Figure 6:
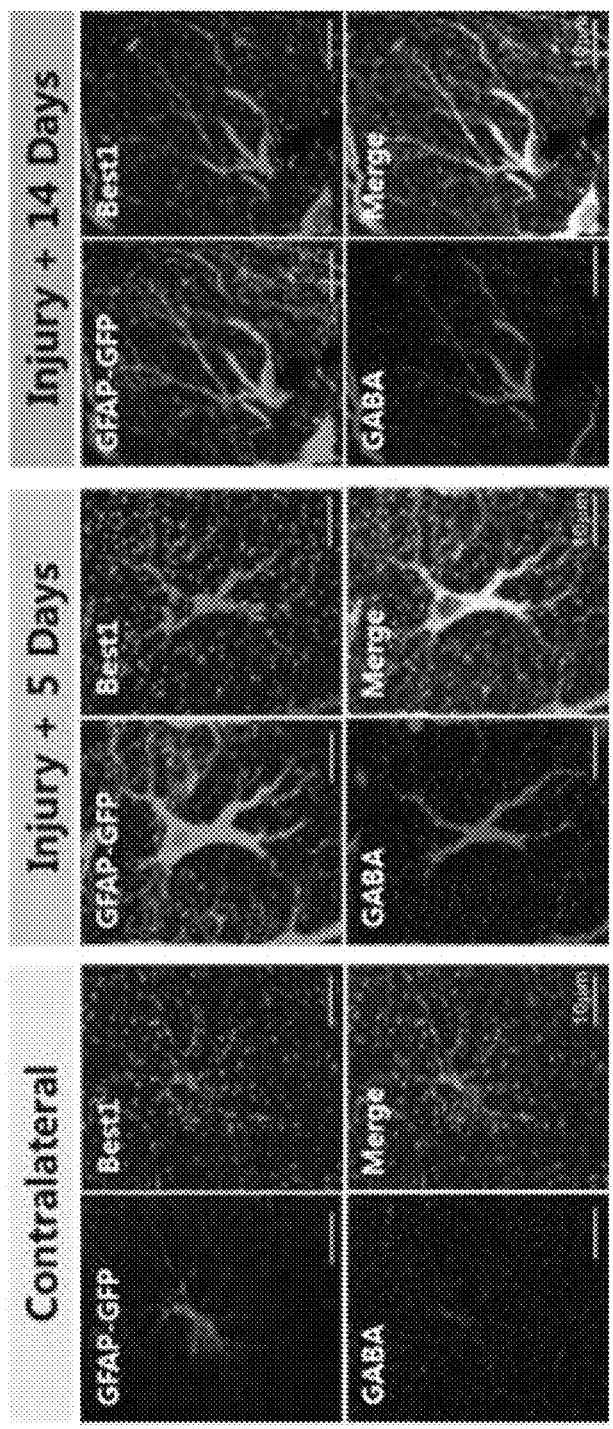
FIG. 6 shows confocal fluorescent images illustrating a subcellular localization pattern of bestrophine 1 channel in the hippocampal reactive astrocytes of a mouse model with a brain injury.
Figure 7:
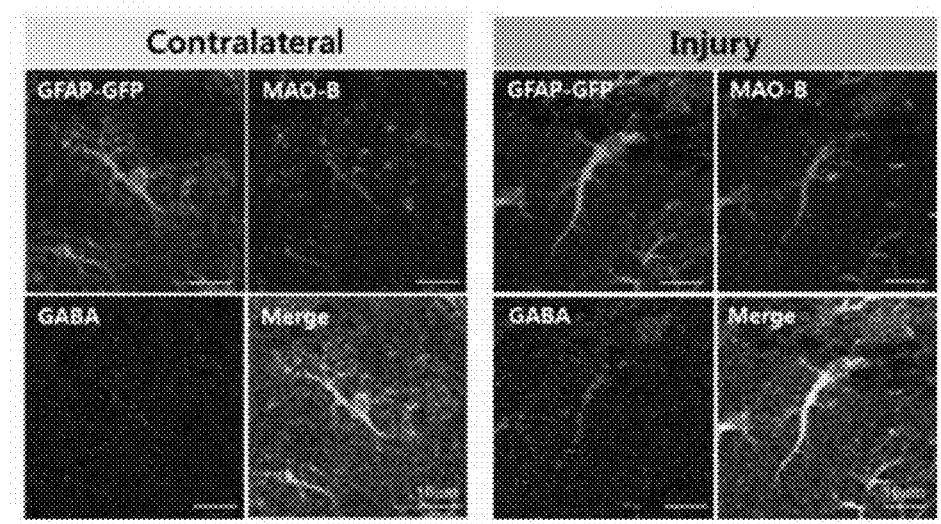
FIG. 7 shows confocal fluorescent images illustrating an amount of expression of MAO-B in the hippocampal reactive astrocytes of the mouse model with a brain injury.
Figure 8:
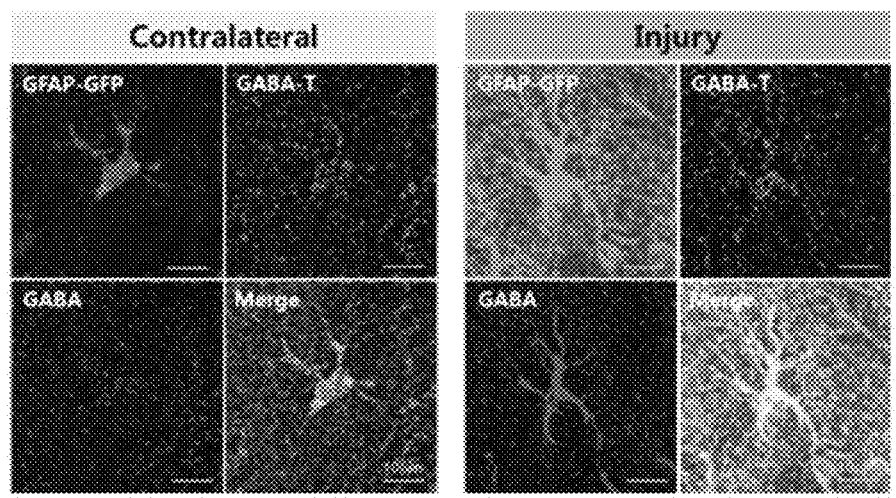
FIG. 8 shows confocal fluorescent images illustrating an amount of expression of a GABA transaminase in the hippocampal reactive astrocytes of the mouse model with a brain injury.

As seen in FIG. 6, similar to an Alzheimer model, the transgenic GFAP-EGFP was found to have an intracellular distribution pattern of bestrophine 1 channel in the reactive astrocytes that gradually changed from micro-domains into cell bodies and main process, and to have an increased expression of MAO-B in the reactive astrocytes 5 days after the hippocampal damage. In addition, on the 5th day after the hippocampal damage, the astrocytic body and main process were found to be larger in size, while an expression of the GABA transaminase per cell area was reduced.

These results indicate that GABA-accumulating reactive astrocytes may be generated with other degenerative brain diseases and brain damage, further to with Alzheimer disease.

Example 5

Preparation of Compound for Screening MAO-B Activity Inhibitory Material

To screen compounds inhibiting the activity of MAO-B associated with the treatment of degenerative brain diseases in the present disclosure as described above in the examples, a total of 79 kinds of compounds were obtained using the following methods:

Example 5-1

Synthesis of N-(2,6-dichloropyridine-3-yl)benzamide

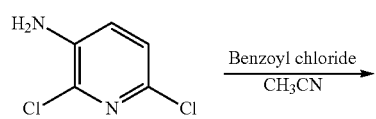

-continued

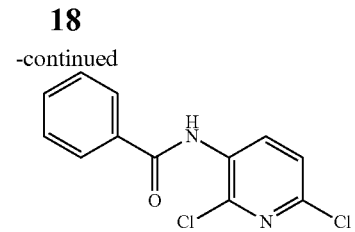

0.038 ml (0.33 mmol) of benzoyl chloride was dissolved in 4 ml of acetonitrile, and 50 mg (0.30 mmol) of 2,6-dichloropyridine-3-amine was added thereto to obtain a mixture, which was then refluxed at about 70° C. for about 6 hours. Termination of the reaction was confirmed by thin layer chromatography (TLC), and the reaction product was cooled to room temperature, followed by distillation under reduced pressure. A small amount of methanol was added to the resulting brown solid so that the color of the brown solid was changed to white. This white solid was filtrated and dried to obtain 58.7 mg (0.22 mmol) of a target compound with a yield of about 73% to 90%.

$^1$H NMR (400 MHz, MeOD) δ 8.29 (d, J=8.4 Hz, 1H), 8.00-7.98 (m, 2H), 7.62 (t, J=6.1 Hz, 1H), 7.57-7.50 (m, 3H)

Example 5-2

Synthesis of 2-chloro-N-(2,6-dichloropyridine-3-yl)benzamide

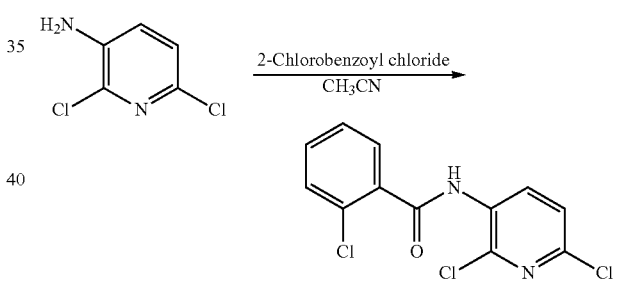

65 mg (0.19 mmol) of a target compound was obtained with a yield of about 75% in the same manner as in Example 5-1, except that 0.04 ml (0.33 mmol) of 2-chlorobenzoyl chloride was used as a starting material.

$^1$H NMR (300 MHz, CDCl$_3$) δ 8.98 (d, J=8.6 Hz, 1H), 8.68 (s, 1H), 7.80 (d, J=6.67 Hz, 1H), 7.56-7.52 (m, 2H), 7.49-7.45 (m, 1H), 7.39 (d, J=8.6 Hz, 1H)

Example 5-3

Synthesis of N-(2,6-dichloropyridine-3-yl)-3-fluorobenzamide

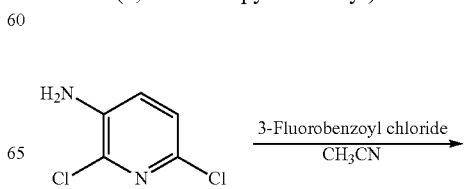

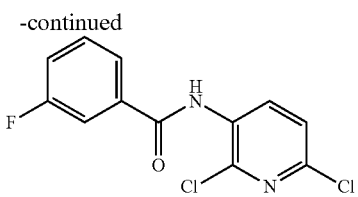

45 mg (0.18 mmol) of a target compound was obtained with a yield of about 60% to 100% in the same manner as in Example 5-1, except that 0.04 ml (0.33 mmol) of 3-fluorobenzoyl chloride was used as a starting material.

$^1$H NMR (300 MHz, CDCl$_3$) δ 8.93 (d, J=8.5 Hz, 1H), 8.37 (s, 1H), 7.68 (t, J=7.5 Hz, 2H), 7.57 (g, J=8.0 Hz, 1H), 7.41-7.34 (m, 2H)

Example 5-4

Synthesis of 3-chloro-N-(2,6-dichloropyridine-3-yl)benzamide

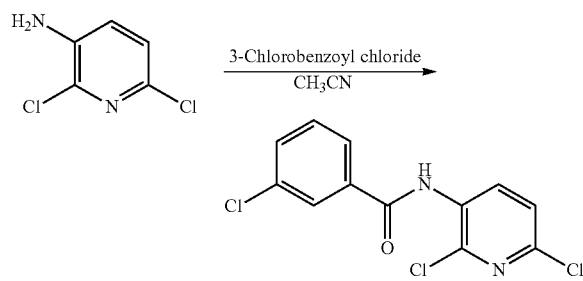

58.8 mg (0.19 mmol) of a target compound was obtained with a yield of about 59% in the same manner as in Example 5-1, except that 0.04 ml (0.33 mmol) of 3-chlorobenzoyl chloride was used as a starting material.

$^1$H NMR (400 MHz, MeOD) δ 8.22 (d, J=8.3 Hz, 1H), 7.97 (t, J=1.9 Hz, 1H), 7.90-7.88 (m, 1H), 7.62-7.61 (m, 1H), 7.5 (dd, J=7.9, 11.6 Hz, 2H)

Example 5-5

Synthesis of N-(2,6-dichloropyridine-3-yl)-3-methylbenzamide

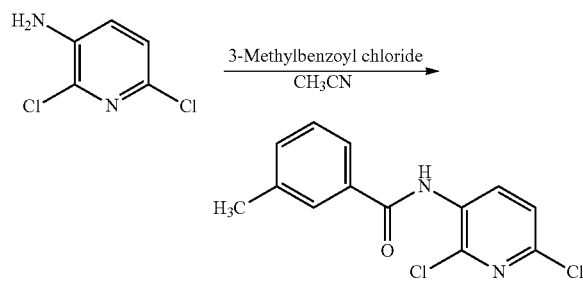

1 g (3.6 mmol) of a target compound was obtained with a yield of about 83% in the same manner as in Example 5-1, except that 0.63 ml (4.7 mmol) of 3-methylbenzoyl chloride was used as a starting material.

$^1$H NMR (300 MHz, CDCl$_3$) δ 8.92 (d, J=8.4 Hz, 1H), 8.36 (s, 1H), 7.72 (s, 1H), 7.70-7.67 (m, 1H), 7.43 (d, J=4.2 Hz, 1H), 7.35 (d, J=3.3 Hz, 1H), 2.47 (s, 3H)

Example 5-6

Synthesis of N-(2,6-dichloropyridine-3-yl)-3-nitrobenzamide 960 mg (3.07 mmol) of a target compound was obtained with a yield of about 99% in the same manner as in Example 5-1, except that 626 mg (3.4 mmol) of 3-nitrobenzoyl chloride was used as a starting material.

$^1$H NMR (300 MHz, CDCl$_3$) δ 8.87 (d, J=8.4 Hz, 1H), 8.77 (s, 1H), 8.49 (dd, J=2.4, 6.0 Hz, 1H), 8.37 (s, 1H), 8.24 (d, J=7.8 Hz, 1H), 7.89 (t, J=8.1 Hz, 1H), 7.58 (d, J=3.6 Hz, 1H)

Example 5-7

Synthesis of 3-cyano-N-(2,6-dichloropyridine-3-yl)benzamide 1.5 g (5.1 mmol) of a target compound was obtained with a yield of about 83% in the same manner as in Example 5-1, except that 1 g (6.1 mmol) of 3-cyanobenzoyl chloride was used as a starting material.

$^1$H NMR (300 MHz, DMSO-d$_6$) δ 8.41 (s, 1H), 8.29 (d, J=10.5 Hz, 1H), 8.18-8.09 (m, 2H), 7.78 (t, J=7.8 Hz, 1H), 7.65 (dd, J=0.9, 7.2 Hz, 1H)

Example 5-8

Synthesis of N-(2,6-dichloropyridine-3-yl)-4-fluorobenzamide

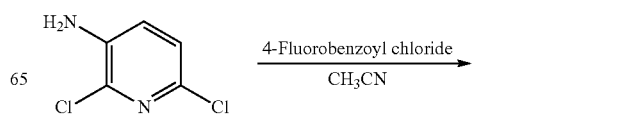

-continued

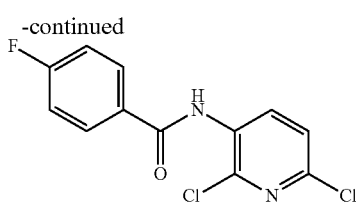

70 mg (0.28 mmol) of a target compound was obtained with a yield of about 94% in the same manner as in Example 5-1, except that 0.04 ml (0.33 mmol) of 4-fluorobenzoyl chloride was used as a starting material.

$^1$H NMR (300 MHz, CDCl$_3$) δ 8.72 (d, J=4.5 Hz, 1H), 8.24 (s, 1H), 7.72 (d, J=8.0 Hz, 2H), 7.46 (d, J=8.1 Hz, 2H), 7.28 (d, J=8.0z, 1H)

Example 5-9

Synthesis of 4-chloro-N-(2,6-dichloropyridine-3-yl)benzamide

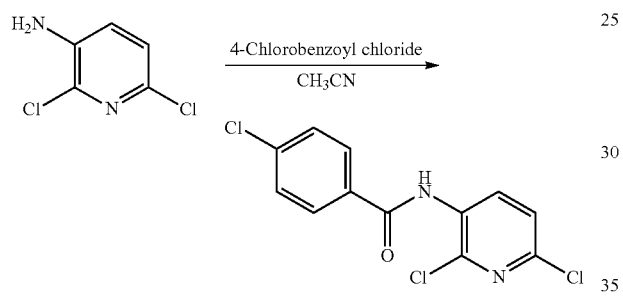

90 mg (0.29 mmol) of a target compound was obtained with a yield of about 99% in the same manner as in Example 5-1, except that 0.04 ml (0.33 mmol) of 4-chlorobenzoyl chloride was used as a starting material.

$^1$H NMR (300 MHz, CDCl$_3$) δ 8.93 (d, J=4.7 Hz, 1H), 8.34 (s, 1H), 7.89 (d, J=8.3 Hz, 2H), 7.56 (d, J=8.3 Hz, 2H), 7.39 (d, J=8.6 Hz, 1H)

Example 5-10

Synthesis of 4-bromo-N-(2,6-dichloropyridine-3-yl)benzamide

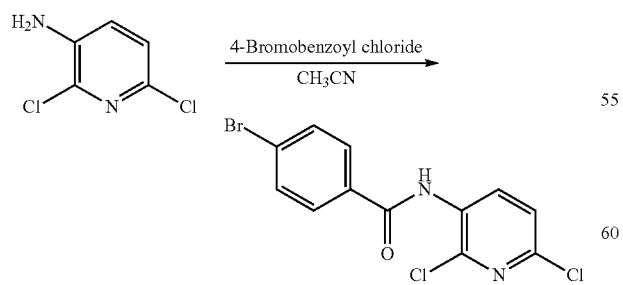

610 mg (1.77 mmol) of a target compound was obtained with a yield of about 56% to 95% in the same manner as in Example 5-1, except that 739 mg (3.37 mmol) of 4-bromobenzoyl chloride was used as a starting material.

$^1$H NMR (300 MHz, MeOD) δ 8.27 (d, J=8.3 Hz, 1H), 7.92-7.89 (m, 2H), 7.76-7.73 (m, 2H), 7.51 (d, J=8.4 Hz, 1H)

Example 5-11

Synthesis of N-(2,6-dichloropyridine-3-yl)-4-methylbenzamide

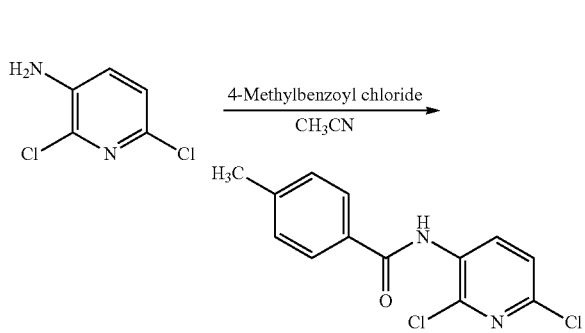

970 mg (3.6 mmol) of a target compound was obtained with a yield of about 80% in the same manner as in Example 5-1, except that 0.63 ml (4.7 mmol) of 4-methylbenzoyl chloride was used as a starting material.

$^1$H NMR (300 MHz, CDCl$_3$) δ 8.97 (d, J=8.6 Hz, 1H), 8.38 (s, 1H), 7.84 (d, J=8.1 Hz, 2H), 7.38 (d, J=8.3 Hz, 3H), 2.49 (s, 3H)

Example 5-12

Synthesis of N-(2,6-dichloropyridine-3-yl)-4-methoxybenzamide

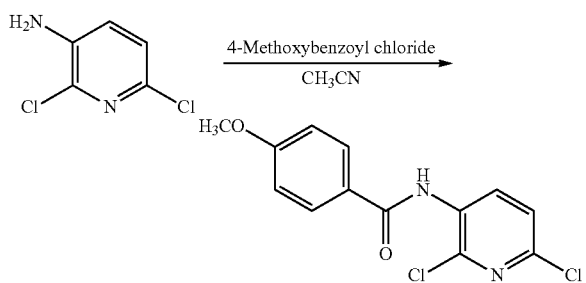

1.8 g (6.0 mmol) of a target compound was obtained with a yield of about 98% in the same manner as in Example 5-1, except that 0.95 ml (6.7 mmol) of 4-methoxybenzoyl chloride was used as a starting material.

$^1$H NMR (300 MHz, CDCl$_3$) δ 8.96 (d, J=8.6 Hz, 1H), 8.33 (s, 1H), 7.94-7.90 (m, 2H), 7.38 (d, J=8.5 Hz, 1H), 7.09-7.04 (m, 2H), 3.94 (s, 3H)

Example 5-13

Synthesis of N-(2,6-dichloropyridine-3-yl)-4-nitrobenzamide

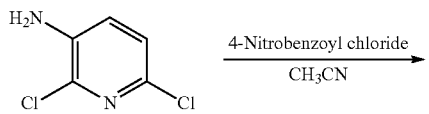

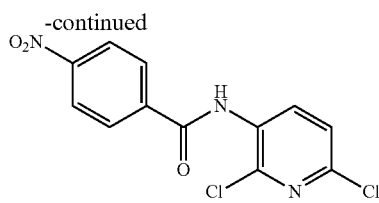

1.6 g (5.2 mmol) of a target compound was obtained with a yield of about 84% in the same manner as in Example 5-1, except that 620 mg (6.7 mmol) of 4-nitrobenzoyl chloride was used as a starting material.

$^1$H NMR (300 MHz, CDCl$_3$) δ 8.93 (d, J=8.6 Hz, 1H), 8.45 (d, J=8.6 Hz, 2H), 8.41 (s, 1H), 8.13 (d, J=8.9 Hz, 2H), 7.43 (d, J=8.6 Hz, 1H)

Example 5-14

Synthesis of 4-cyano-N-(2,6-dichloropyridine-3-yl)benzamide

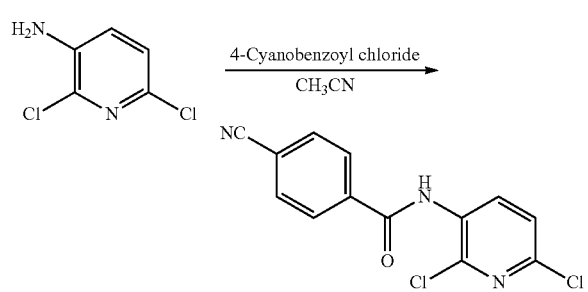

1.7 g (5.9 mmol) of a target compound was obtained with a yield of about 96% in the same manner as in Example 5-1, except that 1.13 ml (6.8 mmol) of 4-cyanobenzoyl chloride was used as a starting material.

$^1$H NMR (300 MHz, CDCl$_3$) δ 8.92 (d, J=8.6 Hz, 1H), 8.38 (s, 1H), 8.05 (d, J=8.3 Hz, 2H), 7.90 (d, J=8.2 Hz, 2H), 7.42 (d, J=8.6 Hz, 1H)

Example 5-15

Synthesis of 5-chloro-2-phenyloxazolo[5,4-b]pyridine

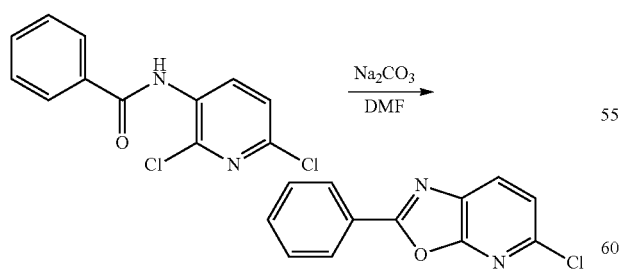

58 mg (0.22 mmol) of N-(2,6-dichloropyridine-3-yl)benzamide and 25 mg of sodium carbonate were added to 2.2 ml of dimethylformamide to obtain a mixture, which was then refluxed at about 160° C. for about 24 hours. Termination of the reaction was confirmed by TLC, and the reaction product was cooled to room temperature and then concentrated under reduced pressure. A small amount of distilled water was added into a resulting concentrated solution, and an aqueous phase was treated with methylene chloride to get an organic phase. The extracted organic phase was dried using anhydrous MgSO$_4$, filtrated, and then concentrated under reduced pressure to obtain a concentrated solution, which was then separated using column chromatography (hexane: ethylacetate=20:1) to obtain 48 mg (0.21 mmol) of a target compound with a yield of about 95%.

$^1$H NMR (300 MHz, CDCl$_3$) δ 8.30 (d, J=6.4 Hz, 2H), 8.05 (d, J=8.2 Hz, 1H), 7.67-7.57 (m, 3H), 7.43 (d, J=8.2 Hz, 1H)

Example 5-16

Synthesis of 5-chloro-2-(2-chlorophenyl)oxazolo[5,4-b]pyridine

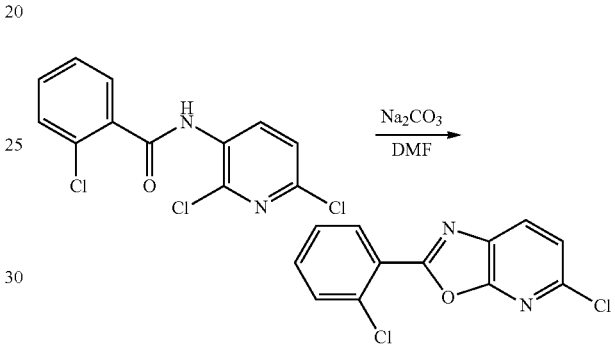

400 mg (1.5 mmol) of a target compound was obtained with a yield of about 75% in the same manner as in Example 5-15, except that 600 mg (2.0 mmol) of 2-chloro-N-(2,6-dichloropyridine-3-yl)benzamide was used as a starting material.

$^1$H NMR (300 MHz, CDCl$_3$) δ 8.20 (d, J=8.6 Hz, 1H), 7.99 (d, J=8.2 Hz, 1H), 7.65 (d, J=8.1 Hz, 1H), 7.45-7.33 (m, 3H)

Example 5-17

Synthesis of 5-chloro-2-(3-fluorophenyl)oxazolo[5,4-b]pyridine

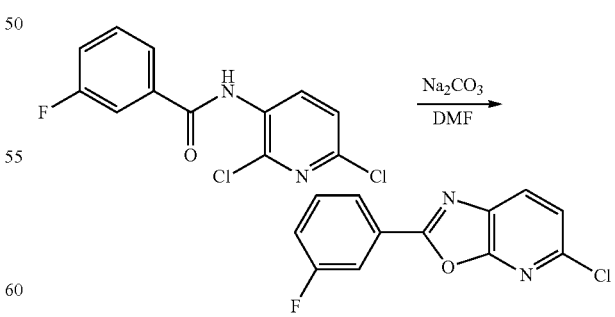

130 mg (0.52 mmol) of a target compound was obtained with a yield of about 51% to about 80% in the same manner as in Example 5-15, except that 300 mg (1.0 mmol) of N-(2,6-dichloropyridine-3-yl)-3-fluorobenzamide was used as a starting material.

¹H NMR (300 MHz, CDCl₃) δ 8.07 (d, J=8.1 Hz, 2H), 7.97 (d, J=9.1 Hz, 1H), 7.57 (q, J=8.0 Hz, 1H), 7.44 (d, J=8.2 Hz, 1H), 7.36-7.30 (m, 1H)

Example 5-18

Synthesis of 5-chloro-2-(3-chlorophenyl)oxazolo[5,4-b]pyridine

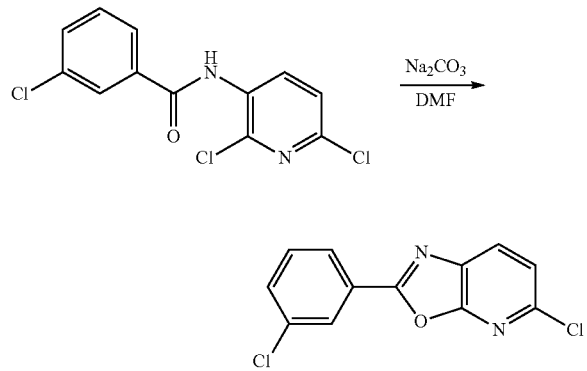

275 mg (1.03 mmol) of a target compound was obtained with a yield of about 63% in the same manner as in Example 5-15, except that 500 mg (1.65 mmol) of 3-chloro-N-(2,6-dichloropyridine-3-yl)benzamide was used as a starting material.

¹H NMR (300 MHz, CDCl₃) δ 8.29 (s, 1H), 8.50 (dd, J=2.9, 4.6 Hz, 1H), 8.06 (d, J=8.2 Hz, 1H), 7.63-7.51 (m, 2H), 7.45 (d, J=8.2 Hz, 1H)

Example 5-19

Synthesis of 5-chloro-2-m-tolyloxazolo[5,4-b]pyridine

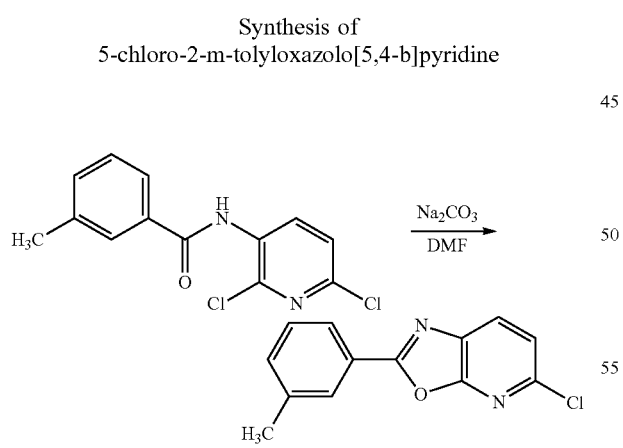

130 mg (0.53 mmol) of a target compound was obtained with a yield of about 76% in the same manner as in Example 5-15, except that 200 mg (0.7 mmol) of N-(2,6-dichloropyridine-3-yl)-3-methylbenzamide was used as a starting material.

¹H NMR (300 MHz, CDCl₃) δ 8.07-7.97 (m, 3H), 7.46-7.32 (m, 3H), 2.46 (s, 3H)

Example 5-20

Synthesis of 5-chloro-2-(3-nitrophenyl)oxazolo[5,4-b]pyridine

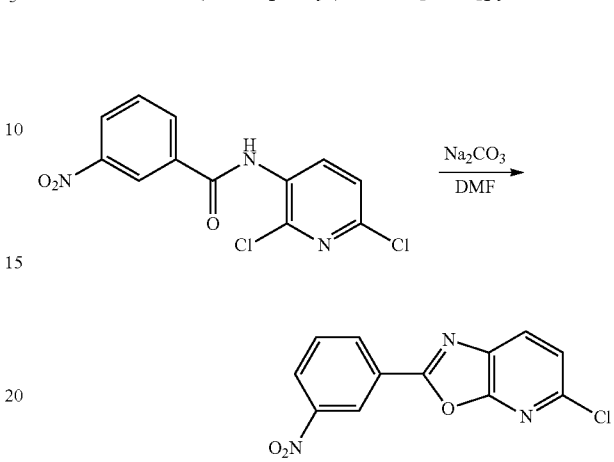

103 mg (0.37 mmol) of a target compound was obtained with a yield of about 50% in the same manner as in Example 5-15, except that 230 mg (0.74 mmol) of N-(2,6-dichloropyridine-3-yl)-3-nitrobenzamide was used as a starting material.

¹H NMR (300 MHz, CDCl₃) δ 9.11 (s, 1H), 8.56 (d, J=5.4 Hz, 1H), 8.44 (d, J=5.1 Hz, 1H), 8.08 (d, J=8.4 Hz, 1H), 7.78 (t, J=8.1 Hz, 1H), 7.45 (d, J=8.4 Hz, 1H)

Example 5-21

Synthesis of 3-(5-chlorooxazolo[5,4-b]pyridine-2-yl)benzonitrile

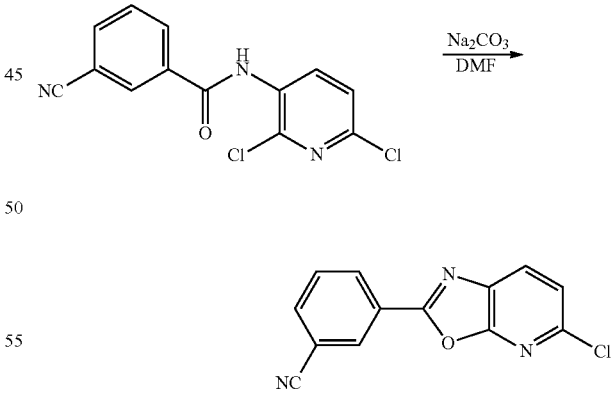

165 mg (0.65 mmol) of a target compound was obtained with a yield of about 38% in the same manner as in Example 5-15, except that 500 mg (1.0 mmol) of 3-cyano-N-(2,6-dichloropyridine-3-yl)benzamide was used as a starting material.

¹H NMR (400 MHz, CDCl₃) δ 8.55 (s, 1H), 8.47 (d, J=5.2 Hz, 1H), 8.06 (d, J=8.2 Hz, 1H), 7.87 (d, J=5.1 Hz, 1H), 7.70 (t, J=7.8 Hz, 1H), 7.44 (d, J=8.2 Hz, 1H)

Example 5-22

Synthesis of 5-chloro-2-(4-fluorophenyl)oxazolo[5,4-b]pyridine

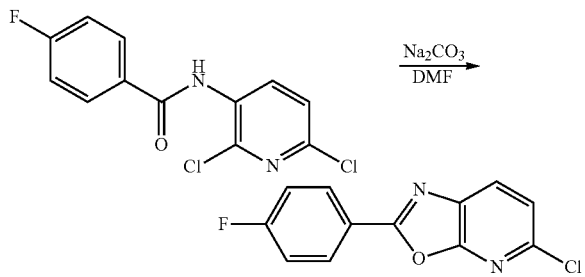

250 mg (1.01 mmol) of a target compound was obtained with a yield of about 73% in the same manner as in Example 5-15, except that 400 mg (1.37 mmol) of N-(2,6-dichloropyridine-3-yl)-4-fluorobenzamide was used as a starting material.

$^1$H NMR (300 MHz, CDCl$_3$) δ 8.32-8.26 (m, 2H), 8.04 (d, J=8.2 Hz, 1H), 7.43 (d, J=8.2 Hz, 1H), 7.32-7.21 (m, 2H)

Example 5-23

Synthesis of 5-chloro-2-(4-chlorophenyl)oxazolo[5,4-b]pyridine

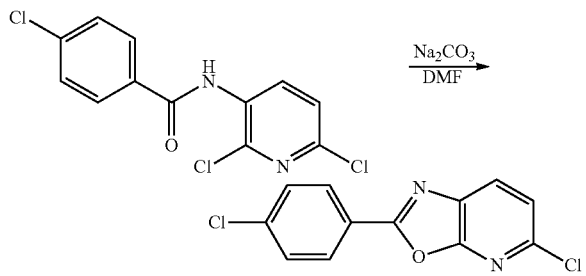

255 mg (0.96 mmol) of a target compound was obtained with a yield of about 60% in the same manner as in Example 5-15, except that 500 mg (1.65 mmol) of 4-chloro-N-(2,6-dichloropyridine-3-yl)benzamide was used as a starting material.

$^1$H NMR (400 MHz, CDCl$_3$) δ 8.51 (dd, J=1.8, 5.1 Hz, 2H), 8.01 (d, J=8.2 Hz, 1H), 7.54 (dd, J=1.8, 5.2 Hz, 2H), 7.40 (d, J=8.2 Hz, 1H)

Example 5-24

Synthesis of 2-(4-bromophenyl)-5-chlorooxazolo[5,4-b]pyridine

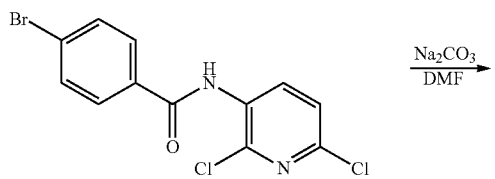

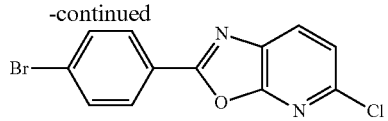

300 mg (0.97 mmol) of a target compound was obtained with a yield of about 57% in the same manner as in Example 5-15, except that 600 mg (1.7 mmol) of 4-bromo-N-(2,6-dichloropyridine-3-yl)benzamide was used as a starting material.

$^1$H NMR (300 MHz, CDCl$_3$) δ 8.15 (d, J=8.6 Hz, 2H), 8.05 (d, J=8.2 Hz, 1H), 7.74 (d, J=8.6 Hz, 2H), 7.44 (d, J=8.2 Hz, 1H)

Example 5-25

Synthesis of 5-chloro-2-p-tolyloxazolo[5,4-b]pyridine

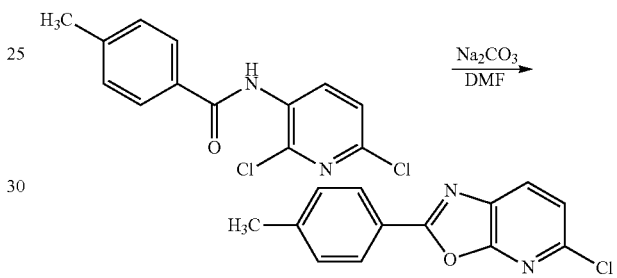

346 mg (1.4 mmol) of a target compound was obtained with a yield of about 88% in the same manner as in Example 5-15, except that 450 mg (1.6 mmol) of N-(2,6-dichloropyridine-3-yl)-4-methylbenzamide was used as a starting material.

$^1$H NMR (300 MHz, CDCl$_3$) δ 8.18 (d, J=8.3 Hz, 2H), 8.02 (d, J=8.2 Hz, 1H), 7.42-7.37 (m, 3H), 2.50 (s, 4H)

Example 5-26

Synthesis of 5-chloro-2-(4-methoxyphenyl)oxazolo[5,4-b]pyridine

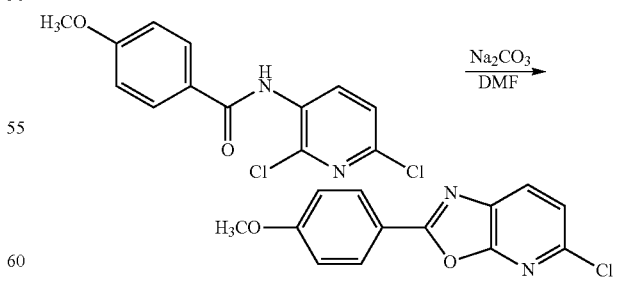

434 mg (1.6 mmol) of a target compound was obtained with a yield of about 72% in the same manner as in Example 5-15, except that 700 mg (2.3 mmol) of N-(2,6-dichloropyridine-3-yl)-4-methoxybenzamide was used as a starting material.

$^1$H NMR (300 MHz, CDCl$_3$) δ 8.23 (dd, J=2.0, 4.9 Hz, 2H), 7.99 (d, J=8.2 Hz, 1H), 7.39 (d, J=8.2 Hz, 1H), 7.09 (dd, J=2.0, 4.9 Hz, 2H), 3.95 (s, 3H)

Example 5-27

Synthesis of 5-chloro-2-(4-nitrophenyl)oxazolo[5,4-b]pyridine

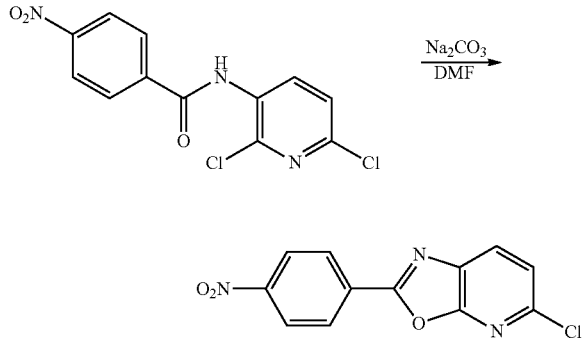

103 mg (0.4 mmol) of a target compound was obtained with a yield of about 51% in the same manner as in Example 5-15, except that 230 mg (0.7 mmol) of N-(2,6-dichloro-pyridine-3-yl)-4-nitrobenzamide was used as a starting material.

$^1$H NMR (300 MHz, CDCl$_3$) δ 8.47 (s, 4H), 8.13 (d, J=8.3 Hz, 1H), 7.50 (d, J=8.3 Hz, 1H)

Example 5-28

Synthesis of 4-(5-chlorooxazolo[5,4-b]pyridine-2-yl)benzonitrile

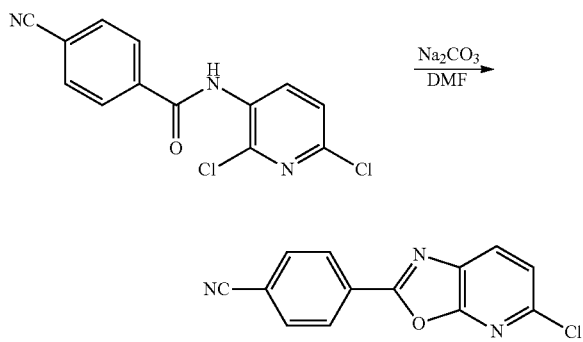

197 mg (0.8 mmol) of a target compound was obtained with a yield of about 45% in the same manner as in Example 5-15, except that 500 mg (1.7 mmol) of 4-cyano-N-(2,6-dichloropyridine-3-yl)benzamide was used as a starting material.

$^1$H NMR (300 MHz, CDCl$_3$) δ 8.41 (d, J=8.3 Hz, 2H), 8.11 (d, J=8.3 Hz, 1H), 7.90 (d, J=8.3 Hz, 2H), 7.49 (d, J=8.3 Hz, 1H)

Example 5-29

Synthesis of 5-chloro-2-phenylthiazolo[5,4-b]pyridine

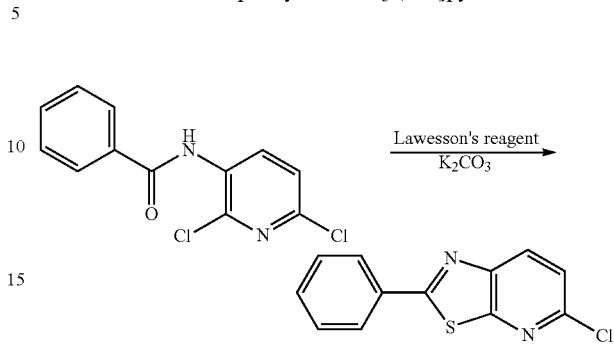

50 mg (0.2 mmol) of N-(2,6-dichloropyridine-3-yl)benzamide and 117 mg (0.3 mmol) of Lawesson's reagent were added to 3 ml of toluene to obtain a mixture, which was then refluxed at about 110° C. for about 5 hours. Termination of the reaction was confirmed by TLC, and the reaction product was cooled to room temperature, and then concentrated under reduced pressure. 80 mg (0.6 mmol) of K2CO3 and 3 ml of dimethylformamide were added into a resulting concentrated solution to obtain a mixture, which was then refluxed at about 160° C. for about 3 hours. Termination of the reaction was confirmed by TLC, and the reaction product was cooled to room temperature. After a small amount of distilled water was added into the reaction product, and an aqueous phase was treated with methylene chloride to get an organic phase. The organic phase was dried using anhydrous Mg2SO4, filtrated, and then concentrated under reduced pressure to obtain a concentrated solution, which was then separated using column chromatography (hexane:ethylacetate=20:1) to obtain 22 mg (0.1 mmol) of a target compound with a yield of about 50% to about 70%.

$^1$H NMR (400 MHz, CDCl$_3$) δ 8.22 (d, J=8.5 Hz, 1H), 8.09-8.07 (m, 2H), 7.55-7.50 (m, 3H), 7.45 (d, J=8.5 Hz, 1H)

Example 5-30

Synthesis of 2-phenyl-5-(pyrrolidine-1-yl)oxazolo[5,4-b]pyridine

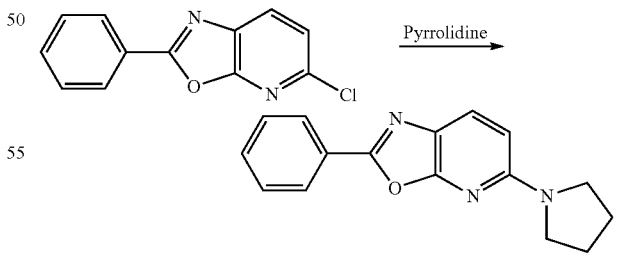

200 mg (0.9 mmol) of 5-chloro-2-phenyloxazolo[5,4-b]pyridine and 10 equivalents of pyrrolidine were added to 1 ml of dimethylformamide to obtain a mixture, which was then refluxed at about 135° C. for about 4 hours. Termination of the reaction was confirmed by TLC, and the reaction product was cooled to room temperature, followed by distillation under reduced pressure to remove pyrrolidine. A saturated NaHCO3 solution was added to the concentrated solution, and an aqueous phase was treated with methylene chloride to obtain an organic phase. The organic phase was dried using anhydrous Na2SO4, filtrated, and concentrated under reduced pressure to obtain a concentrated solution, which was then separated using column chromatography (hexane:ethylacetate=20:1) to obtain 33 mg (0.1 mmol) of a target compound with a yield of about 15%.

$^1$H NMR (300 MHz, CDCl$_3$) δ 8.23-8.20 (m, 2H), 7.82 (d, J=8.7 Hz, 1H), 7.53-7.49 (m, 3H), 6.40 (d, J=8.7 Hz, 1H), 3.56 (t, J=6.7 Hz, 4H), 2.10-2.06 (m, 4H)

Example 5-31

Synthesis of 2-phenyl-5-(pyrrolidine-1-yl)thiazolo[5,4-b]pyridine

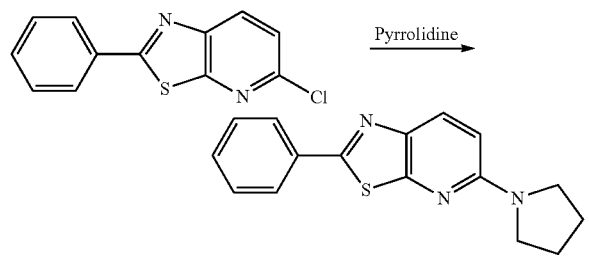

74 mg (0.3 mmol) of a target compound was obtained with a yield of about 65% in the same manner as in Example 5-30, except that 100 mg (0.4 mmol) of 5-chloro-2-phenylthiazolo[5,4-b]pyridine was used as a starting material.

$^1$H NMR (300 MHz, CDCl$_3$) δ 8.03 (d, J=8.9 Hz, 3H), 7.50-7.45 (m, 3H), 6.54 (d, J=9.0 Hz, 1H), 3.58 (t, J=6.7 Hz, 4H), 2.10-2.05 (m, 4H)

Example 5-32

Synthesis of 2-chlorophenyl-5-(pyrrolidine-1-yl)oxazolo[5,4-b]pyridine

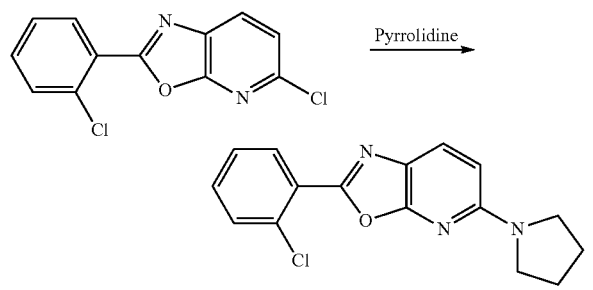

38 mg (0.13 mmol) of a target compound was obtained with a yield of about 32% in the same manner as in Example 5-30, except that 100 mg (0.4 mmol) of 5-chloro-2-(2-chlorophenyl)oxazolo[5,4-b]pyridine was used as a starting material.

$^1$H NMR (300 MHz, CDCl$_3$) δ 8.21-8.16 (m, 1H), 7.91 (d, J=8.7 Hz, 1H), 7.60-7.54 (m, 1H), 7.44-7.38 (m, 2H), 6.43 (d, J=8.8 Hz, 1H), 3.58 (s, 4H), 2.08 (s, 4H)

Example 5-33

Synthesis of 2-chlorophenyl-5-(pyrrolidine-1-yl)oxazolo[5,4-b]pyridine

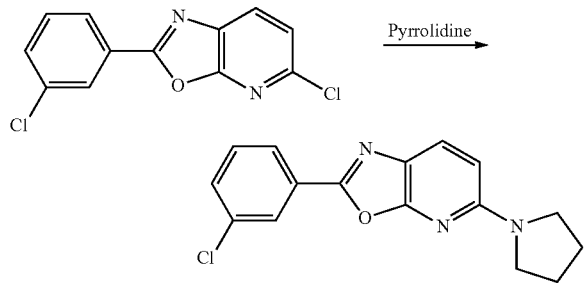

30 mg (0.1 mmol) of a target compound was obtained with a yield of about 26% in the same manner as in Example 5-30, except that 100 mg (0.4 mmol) of 5-chloro-2-(3-chlorophenyl)oxazolo[5,4-b]pyridine was used as a starting material.

$^1$H NMR (300 MHz, CDCl$_3$) δ 8.22 (s, 1H), 8.09-8.06 (m, 1H), 7.82 (d, J=8.7 Hz, 1H), 7.46-7.44 (m, 2H), 6.42 (d, J=8.7 Hz, 1H), 3.57 (t, J=6.6 Hz, 4H), 2.11-2.07 (m, 4H)

Example 5-34

Synthesis of 2-fluorophenyl-5-(pyrrolidine-1-yl)oxazolo[5,4-b]pyridine

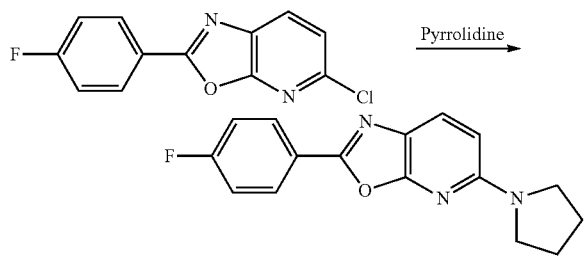

25 mg (0.1 mmol) of a target compound was obtained with a yield of about 22% in the same manner as in Example 5-30, except that 100 mg (0.4 mmol) of 5-chloro-2-(4-fluorophenyl)oxazolo[5,4-b]pyridine was used as a starting material.

$^1$H NMR (300 MHz, CDCl$_3$) δ 8.11 (d, J=8.9 Hz, 2H), 7.90 (d, J=8.1 Hz, 1H), 7.34-7.32 (m, 1H), 6.67 (d, J=8.9 Hz, 2H), 3.44 (t, J=6.6 Hz, 4H), 2.12-2.09 (m, 4H)

Example 5-35

Synthesis of 2-chlorophenyl-5-(pyrrolidine-1-yl)oxazolo[5,4-b]pyridine

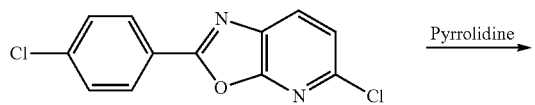

-continued

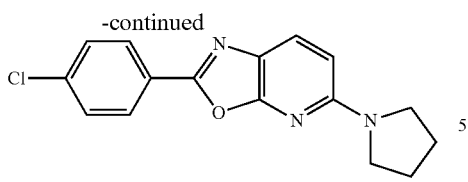

40 mg (0.13 mmol) of a target compound was obtained with a yield of about 34% in the same manner as in Example 5-30, except that 100 mg (0.4 mmol) of 5-chloro-2-(4-chlorophenyl)oxazolo[5,4-b]pyridine was used as a starting material.

$^1$H NMR (300 MHz, CDCl$_3$) δ 8.16-8.12 (m, 2H), 7.84-7.80 (m, 1H), 7.51-7.47 (m, 2H), 7.30 (s, 1H), 6.44 (m, 1H), 3.57 (d, J=4.4 Hz, 4H), 2.09 (d, J=4.7 Hz, 4H)

Example 5-36

Synthesis of 2-bromophenyl-5-(pyrrolidine-1-yl)oxazolo[5,4-b]pyridine

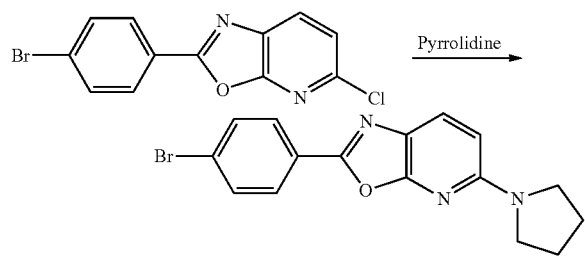

20 mg (0.06 mmol) of a target compound was obtained with a yield of about 15% in the same manner as in Example 2-30, except that 100 mg (0.4 mmol) of 2-(4-bromophenyl)-5-chlorooxazolo[5,4-b]pyridine was used as a starting material.

$^1$H NMR (300 MHz, CDCl$_3$) δ 8.06 (d, J=8.6 Hz, 2H), 7.81 (d, J=8.7 Hz, 1H), 7.64 (d, J=8.6 Hz, 2H), 6.40 (d, J=8.7 Hz, 1H), 3.56 (t, J=6.5 Hz, 4H), 2.11-2.06 (m, 4H)

Example 5-37

Synthesis of 2-phenyl-5-(piperidine-1-yl)oxazolo[5,4-b]pyridine

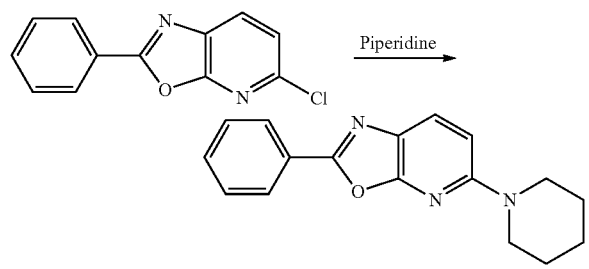

28 mg (0.1 mmol) of a target compound was obtained with a yield of about 26% in the same manner as in Example 5-30, except that 100 mg (0.4 mmol) of 5-chloro-2-phenyloxazolo[5,4-b]pyridine and 10 equivalents of piperidine were used as starting materials.

$^1$H NMR (300 MHz, CDCl$_3$) δ 8.22-8.16 (m, 2H), 7.80 (d, J=8.7 Hz, 1H), 7.83-7.47 (m, 3H), 6.70 (d, J=8.7 Hz, 1H), 3.63 (s, 4H), 1.68 (s, 6H)

Example 5-38

Synthesis of 2-phenyl-5-(piperidine-1-yl)thiazolo[5,4-b]pyridine

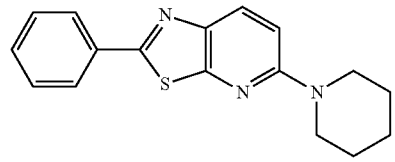

83 mg (0.3 mmol) of a target compound was obtained with a yield of about 73% in the same manner as in Example 5-30, except that 100 mg (0.4 mmol) of 5-chloro-2-phenylthiazolo[5,4-b]pyridine was used as a starting material.

$^1$H NMR (300 MHz, CDCl$_3$) δ 8.04 (d, J=9.2 Hz, 3H), 7.51-7.48 (m, 3H), 6.84 (d, J=9.2 Hz, 1H), 3.67 (s, 4H), 1.71 (s, 6H)

Example 5-39

Synthesis of 2-chlorophenyl-5-(piperidine-1-yl)oxazolo[5,4-b]pyridine

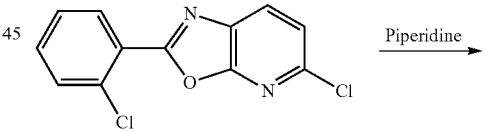

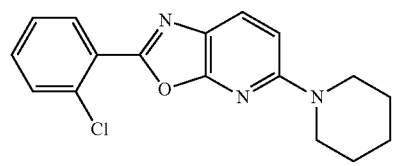

21 mg (0.06 mmol) of a target compound was obtained with a yield of about 18% in the same manner as in Example 5-30, except that 100 mg (0.4 mmol) of 5-chloro-2-(2-chlorophenyl)oxazolo[5,4-b]pyridine was used as a starting material.

$^1$H NMR (300 MHz, CDCl$_3$) δ 8.19-8.16 (m, 1H), 7.91 (d, J=8.9 Hz, 1H), 7.59-7.56 (m, 1H), 7.44-7.41 (m, 2H), 6.73 (d, J=8.9 Hz, 1H), 3.67 (s, 4H), 1.72 (s, 6H)

Example 5-40

Synthesis of 2-(3-fluorophenyl)-5-(piperidine-1-yl)oxazolo[5,4-b]pyridine

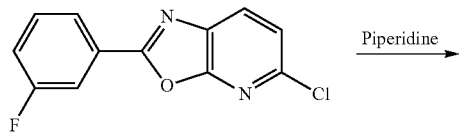

23 mg (0.1 mmol) of a target compound was obtained with a yield of about 19% in the same manner as in Example 5-30, except that 100 mg (0.4 mmol) of 5-chloro-2-(3-fluorophenyl)oxazolo[5,4-b]pyridine was used as a starting material.

$^1$H NMR (300 MHz, CDCl$_3$) δ 8.00 (d, J=7.8 Hz, 1H), 7.90 (d, J=8.0 Hz, 1H), 7.84 (d, J=8.9 Hz, 1H), 7.53-7.18 (m, 1H0, 7.21 (t, J=5.9 Hz, 1H), 6.73 (d, J=8.9 Hz, 1H), 3.67 (s, 4H), 1.72 (s, 6H)

Example 5-41

Synthesis of 2-chlorophenyl-5-(piperidine-1-yl)oxazolo[5,4-b]pyridine

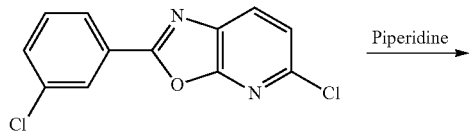

67 mg (0.2 mmol) of a target compound was obtained with a yield of about 56% in the same manner as in Example 5-30, except that 100 mg (0.4 mmol) of 5-chloro-2-(3-chlorophenyl)oxazolo[5,4-b]pyridine was used as a starting material.

$^1$H NMR (300 MHz, CDCl$_3$) δ 8.22 (s, 1H), 8.09 (d, J=6.5 Hz, 1H), 7.84 (d, J=8.8 Hz, 1H), 7.47 (s, 2H), 6.72 (d, J=8.9 Hz, 1H), 3.67 (s, 4H), 1.72 (s, 6H)

Example 5-42

Synthesis of 5-(piperidine-1-yl)-2-m-tolyloxazolo[5,4-b]pyridine

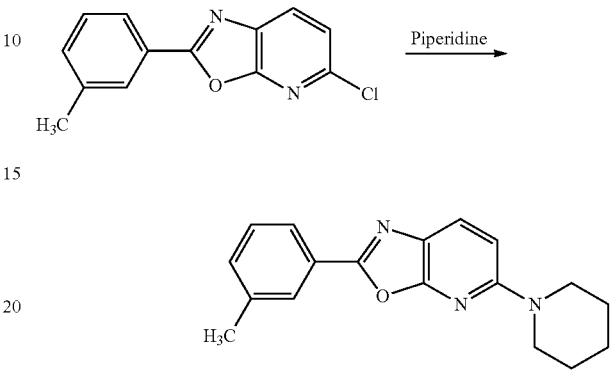

61 mg (0.2 mmol) of a target compound was obtained with a yield of about 52% in the same manner as in Example 5-30, except that 100 mg (0.4 mmol) of 5-chloro-2-m-tolyloxazolo[5,4-b]pyridine was used as a starting material.

$^1$H NMR (300 MHz, CDCl$_3$) δ 8.07 (s, 1H), 8.02 (d, J=7.7 Hz, 1H), 7.41 (t, J=7.6 Hz, 1H), 7.32 (d, J=7.6 Hz, 1H), 3.66 (s, 4H), 2.47 (s, 3H), 1.72 (s, 6H)

Example 5-43

Synthesis of 2-nitrophenyl-5-(piperidine-1-yl)oxazolo[5,4-b]pyridine

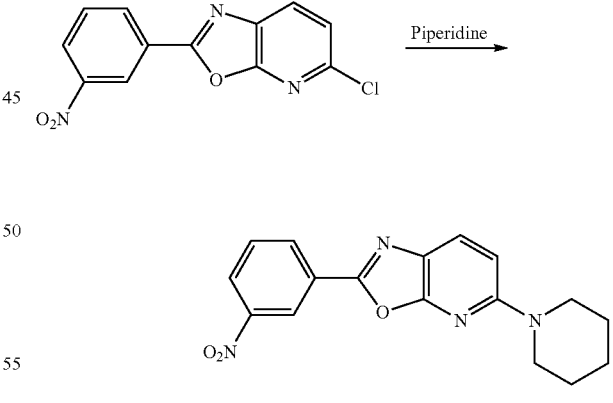

39 mg (0.12 mmol) of a target compound was obtained with a yield of about 30% in the same manner as in Example 5-30, except that 100 mg (0.4 mmol) of 5-chloro-2-(3-nitrophenyl)oxazolo[5,4-b]pyridine was used as a starting material.

$^1$H NMR (300 MHz, CDCl$_3$) δ 9.06 (s, 1H), 8.51 (d, J=7.8 Hz, 1H), 8.35 (d, J=5.0 Hz, 1H), 7.87 (d, J=8.9 Hz, 1H), 7.71 (t, J=8.0 Hz, 1H), 6.75 (d, J=8.9 Hz, 1H), 3.70 (s, 4H), 1.73 (s, 6H)

Example 5-44

Synthesis of 3-(5-(piperidine-1-yl)oxazolo[5,4-b]pyridine-2-yl)benzonitrile

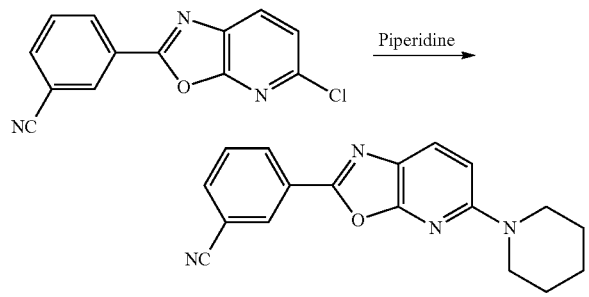

26 mg (0.09 mmol) of a target compound was obtained with a yield of about 22% in the same manner as in Example 5-30, except that 100 mg (0.4 mmol) of 3-(5-chlorooxazolo[5,4-b]pyridine-2-yl)benzonitrile was used as a starting material.

$^1$H NMR (300 MHz, CDCl$_3$) δ 8.50 (s, 1H), 8.42 (d, J=5.3 Hz, 1H), 7.85 (d, J=8.9 Hz, 1H), 7.78 (d, J=3.56 Hz, 1H), 7.65 (t, J=7.9H z, 1H), 6.75 (d, J=8.9 Hz, 1H), 3.71 (s, 4H), 1.73 (s, 6H)

Example 5-45

Synthesis of 2-(4-fluorophenyl)-5-(piperidine-1-yl)oxazolo[5,4-b]pyridine

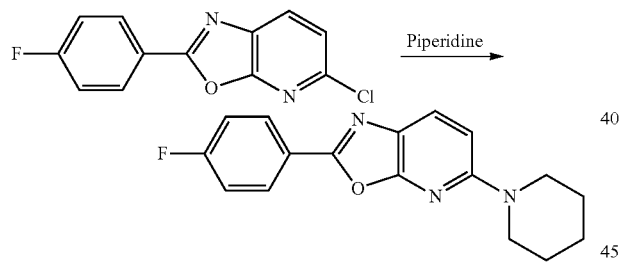

20 mg (0.1 mmol) of a target compound was obtained with a yield of about 11% in the same manner as in Example 5-30, except that 100 mg (0.4 mmol) of 5-chloro-2-(4-fluorophenyl)oxazolo[5,4-b]pyridine was used as a starting material.

$^1$H NMR (300 MHz, CDCl$_3$) δ 8.11 (d, J=9.1 Hz, 2H), 7.92 (d, J=8.2 Hz, 1H), 7.33 (t, J=8.1 Hz, 1H), 7.36 (d, J=9.1 Hz, 2H), 3.43 (s, 4H), 1.72 (s, 6H)

Example 5-46

Synthesis of 2-chlorophenyl-5-(piperidine-1-yl)oxazolo[5,4-b]pyridine

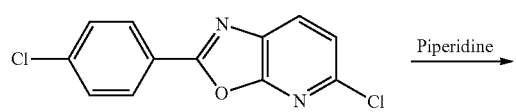

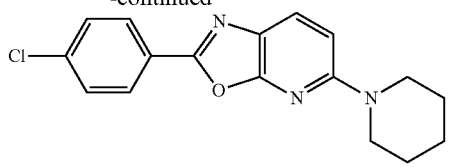

30 mg (0.1 mmol) of a target compound was obtained with a yield of about 17% in the same manner as in Example 5-30, except that 150 mg (0.6 mmol) of 5-chloro-2-(4-chlorophenyl)oxazolo[5,4-b]pyridine was used as a starting material.

$^1$H NMR (300 MHz, CDCl$_3$) δ 8.14 (d, J=8.7 Hz, 2H), 7.83 (d, J=8.9 Hz, 1H), 7.50 (d, J=8.7 Hz, 2H), 6.72 (d, J=8.9 Hz, 1H), 3.67 (s, 4H), 1.72 (s, 6H)

Example 5-47

Synthesis of 2-(4-bromophenyl)-5-(piperidine-1-yl)oxazolo[5,4-b]pyridine

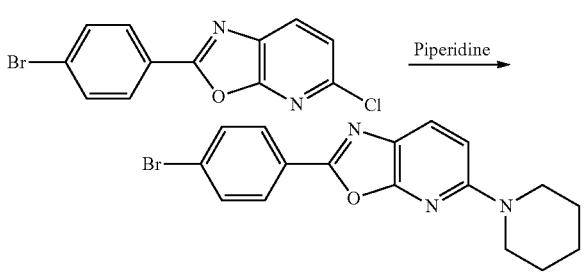

40 mg (0.1 mmol) of a target compound was obtained with a yield of about 23% in the same manner as in Example 2-30, except that 150 mg (0.5 mmol) of 2-(4-bromophenyl)-5-chlorooxazolo[5,4-b]pyridine was used as a starting material.

$^1$H NMR (300 MHz, CDCl$_3$) δ 8.11 (d, J=9.1 Hz, 2H), 7.92 (d, J=8.2 Hz, 1H), 7.33 (t, J=8.1 Hz, 1H), 7.35 (d, J=9.1 Hz, 2H), 3.43 (s, 4H), 1.72 (s, 6H)

Example 5-48

Synthesis of 5-(piperidine-1-yl)-2-p-tolyloxazolo[5,4-b]pyridine

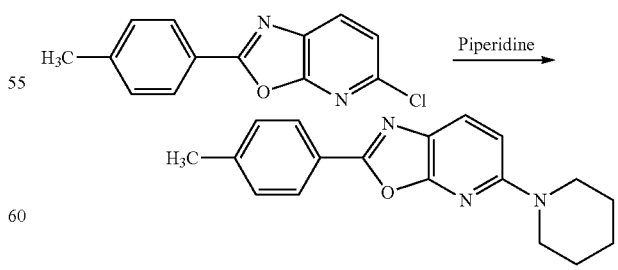

30 mg (0.1 mmol) of a target compound was obtained with a yield of about 25% in the same manner as in Example 5-30, except that 100 mg (0.4 mmol) of 5-chloro-2-p-tolyloxazolo[5,4-b]pyridine was used as a starting material.

¹H NMR (300 MHz, CDCl₃) δ 8.11 (d, J=8.2 Hz, 2H), 7.83 (d, J=8.8 Hz, 1H), 7.34 (d, J=8.0 Hz, 2H), 6.70 (d, J=8.8 Hz, 1H), 3.66 (s, 4H), 2.46 (s, 3H), 1.72 (s, 6H)

Example 5-49

Synthesis of 2-(4-methoxyphenyl)-5-(piperidine-1-yl)oxazolo[5,4-b]pyridine

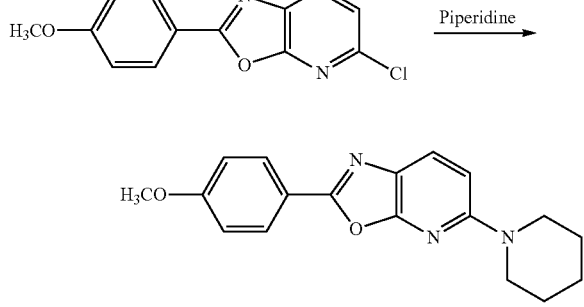

20 mg (0.06 mmol) of a target compound was obtained with a yield of about 17% in the same manner as in Example 5-30, except that 100 mg (0.4 mmol) of 5-chloro-2-(4-methoxyphenyl)oxazolo[5,4-b]pyridine was used as a starting material.

¹H NMR (300 MHz, CDCl₃) δ 8.15 (d, J=9.0 Hz, 2H), 7.80 (d, J=8.8 Hz, 1H), 7.04 (dd, J=2.8, 6.9 Hz, 2H), 6.69 (d, J=8.8 Hz, 1H), 3.91 (s, 3H), 3.64 (s, 4H), 1.71 (s, 6H)

Example 5-50

Synthesis of 4-(5-(piperidine-1-yl)oxazolo[5,4-b]pyridine-2-yl)benzonitrile

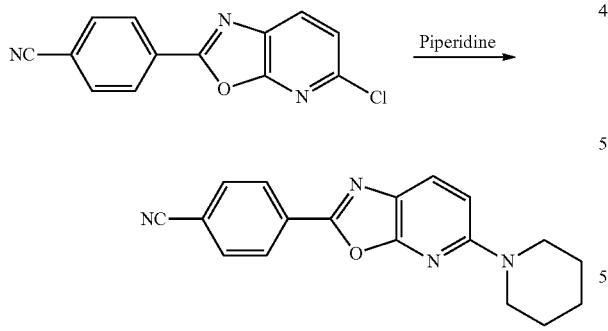

18 mg (0.06 mmol) of a target compound was obtained with a yield of about 15% in the same manner as in Example 5-30, except that 100 mg (0.4 mmol) of 4-(5-chlorooxazolo[5,4-b]pyridine-2-yl)benzonitrile was used as a starting material.

¹H NMR (300 MHz, CDCl₃) δ 8.30 (d, J=8.5 Hz, 2H), 7.83 (q, J=8.9 Hz, 3H), 6.75 (d, J=8.9 Hz, 1H), 3.70 (s, 4H), 1.73 (s, 6H)

Example 5-51

Synthesis of 2-(3-chlorophenyl)-N-cyclopentyloxazolo[5,4-b]pyridine-5-amine

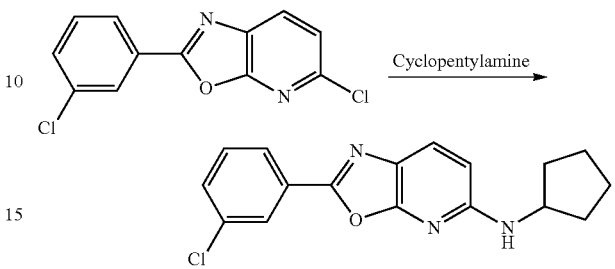

18 mg (0.06 mmol) of a target compound was obtained with a yield of about 15% in the same manner as in Example 5-30, except that 100 mg (0.4 mmol) of 5-chloro-2-(3-chlorophenyl)oxazolo[5,4-b]pyridine and 10 equivalents of cyclopentylamine were used as starting materials.

¹H NMR (300 MHz, CDCl₃) δ 8.21 (s, 1H), 8.10-8.06 (m, 1H), 7.80 (d, J=8.6 Hz, 1H), 7.50-7.45 (m, 2H), 6.44 (d, J=8.6 Hz, 1H), 4.75 (d, J=6.2 Hz, 1H), 4.25-4.19 (m, 1H), 2.21-2.11 (m, 2H), 1.83-1.68 (m, 4H), 1.58-1.50 (m, 2H)

Example 5-52

Synthesis of N-cyclohexyl-2-phenylthiazolo[5,4-b]pyridine-5-amine

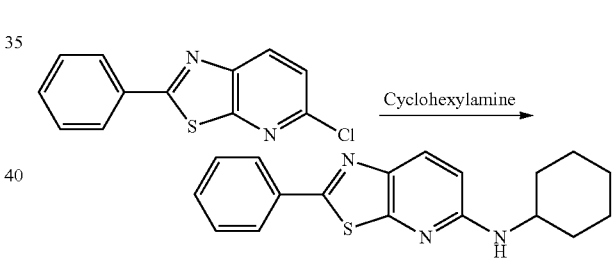

10 mg (0.03 mmol) of a target compound was obtained with a yield of about 9% in the same manner as in Example 5-30, except that 99 mg (0.4 mmol) of 5-chloro-2-phenylthiazolo[5,4-b]pyridine and 10 equivalents of cyclopentylamine were used as starting materials.

¹H NMR (300 MHz, CDCl₃) δ 8.03-7.99 (m, 3H), 7.48 (s, 3H), 6.53 (d, J=8.9 Hz, 1H), 4.68 (d, J=6.4 Hz, 1H), 3.75 (t, J=3.4 Hz, 1H), 2.13 (d, J=12.1 Hz, 2H), 1.84-1.80 (m, 2H), 1.73-1.69 (m, 1H), 1.54-1.42 (m, 2H), 1.33-1.22 (m, 3H)

Example 5-53

Synthesis of 2-(3-chlorophenyl)-N-cyclohexyloxazolo[5,4-b]pyridine-5-amine

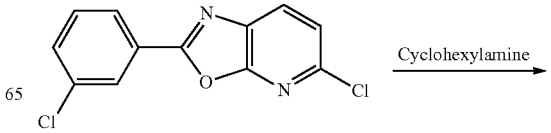

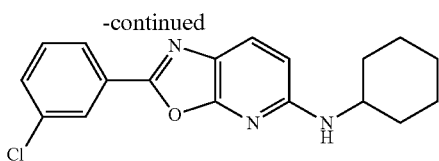

24 mg (0.07 mmol) of a target compound was obtained with a yield of about 19% in the same manner as in Example 5-30, except that 100 mg (0.4 mmol) of 5-chloro-2-(3-chlorophenyl)oxazolo[5,4-b]pyridine was used as a starting material.

$^1$H NMR (300 MHz, MeOD) δ 8.07 (s, 1H), 8.03-8.00 (m, 1H0, 7.68 (d, J=8.7 Hz, 1H), 7.54-7.51 (m, 2H), 6.53 (d, J=8.7 Hz, 1H), 3.79-3.75 (m, 1H), 2.06 (d, J=9.7 Hz, 2H), 1.82 (d, J=6.2 Hz, 2H), 1.70 (d, J=3.6 Hz, 1H), 1.54-1.40 (m, 2H), 1.33-1.25 (m, 3H)

Example 5-54

Synthesis of 5-(azepane-1-yl)-2-phenyloxazolo[5,4-b]pyridine

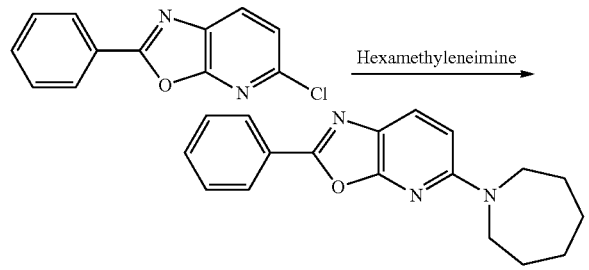

70 mg (0.2 mmol) of a target compound was obtained with a yield of about 57% in the same manner as in Example 5-30, except that 97 mg (0.4 mmol) of 5-chloro-2-phenyloxazolo[5,4-b]pyridine and 10 equivalents of hexamethyleneimine were used as starting materials.

$^1$H NMR (300 MHz, CDCl$_3$) δ 8.24-8.20 (m, 2H), 7.82 (d, J=8.8 Hzm 1H), 7.54-7.50 (m, 3H), 6.54 (d, J=8.9 Hz, 1H), 3.74 (t, J=5.9 Hz, 4H), 1.88 (s, 4H), 1.63-1.59 (m, 4H)

Example 5-55

Synthesis of 5-(azepane-1-yl)-2-phenylthiazolo[5,4-b]pyridine

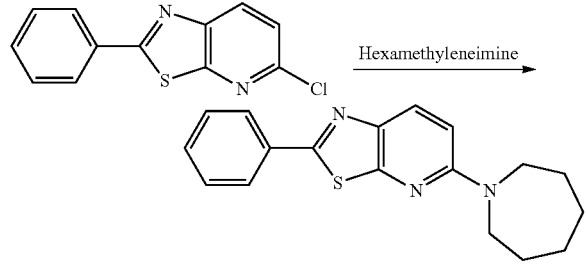

51 mg (0.2 mmol) of a target compound was obtained with a yield of about 47% in the same manner as in Example 5-30, except that 85 mg (0.35 mmol) of 5-chloro-2-phenylthiazolo[5,4-b]pyridine was used as a starting material.

$^1$H NMR (300 MHz, CDCl$_3$) δ 8.05-8.00 (m, 3H), 7.50-7.48 (m, 3H), 6.68 (d, J=9.2 Hz, 1H), 3.75 (t, J=5.9 Hz, 4H), 1.87 (s, 4H), 1.63-1.59 (m, 4H)

Example 5-56

Synthesis of 5-(azepane-1-yl)-2-(4-fluorophenyl) oxazolo[5,4-b]pyridine

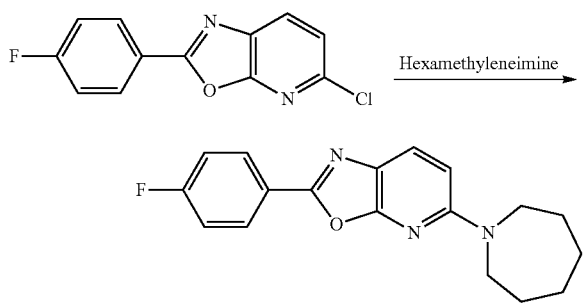

29 mg (0.1 mmol) of a target compound was obtained with a yield of about 23% in the same manner as in Example 5-30, except that 100 mg (0.4 mmol) of 5-chloro-2-(4-fluorophenyl)oxazolo[5,4-b]pyridine was used as a starting material.

$^1$H NMR (300 MHz, CDCl$_3$) δ 8.23-8.18 (m, 2H), 7.80 (d, J=8.8 Hz, 1H), 7.20 (t, J=8.7 Hz, 2H), 6.54 (d, J=8.9 Hz, 1H0, 3.73 (t, J=5.9 Hz, 4H), 1.88 (s, 4H), 1.63-1.60 (m, 4H)

Example 5-57

Synthesis of N-benzyl-2-phenyloxazolo[5,4-b]pyridine-5-amine

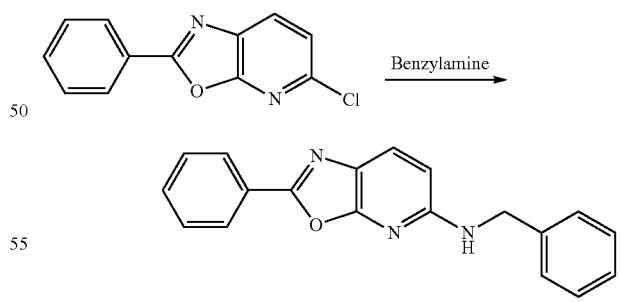

30 mg (0.1 mmol) of a target compound was obtained with a yield of about 25% in the same manner as in Example 5-30, except that 97 mg (0.4 mmol) of 5-chloro-2-phenyloxazolo[5,4-b]pyridine and 10 equivalents of benzylamine were used as starting materials.

$^1$H NMR (300 MHz, CDCl$_3$) δ 8.24-8.21 (m, 2H), 7.82 (d, J=8.6 Hz, 1H), 7.55-7.51 (m, 3H), 7.46-7.31 (m, 5H), 6.46 (d, J=8.6 Hz, 1H), 5.04 (s, 1H), 4.67 (d, J=5.7 Hz, 2H)

Example 5-58

Synthesis of N-benzyl-2-phenylthiazolo[5,4-b]pyridine-5-amine

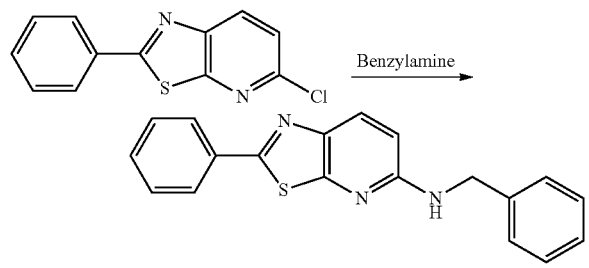

49 mg (0.2 mmol) of a target compound was obtained with a yield of about 65% in the same manner as in Example 5-30, except that 60 mg (0.24 mmol) of 5-chloro-2-phenylthiazolo[5,4-b]pyridine was used as a starting material.

$^1$H NMR (300 MHz, CDCl$_3$) δ 8.06-8.00 (m, 3H), 7.54-7.31 (m, 8H), 6.57 (d, J=8.9 Hz, 1H), 5.10 (s, 1H), 4.67 (d, J=5.7 Hz, 2H)

Example 5-59

Synthesis of N-benzyl-2-(3-fluorophenyl)oxazolo[5,4-b]pyridine-5-amine

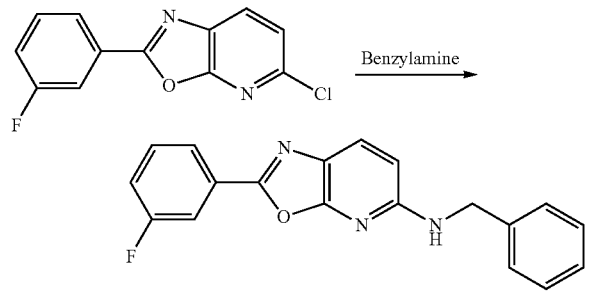

30 mg (0.1 mmol) of a target compound was obtained with a yield of about 35% in the same manner as in Example 5-30, except that 70 mg (0.3 mmol) of 5-chloro-2-(3-fluorophenyl)oxazolo[5,4-b]pyridine was used as a starting material.

$^1$H NMR (300 MHz, CDCl$_3$) δ 8.00 (d, J=7.8 Hz, 1H), 7.93-7.88 (m, 1H), 7.82 (d, J=8.6 Hz, 1H), 7.54-7.32 (m, 6H), 7.26-7.19 (m, 1H), 6.48 (d, J=8.6 Hz, 1H), 5.07 (s, 1H), 4.67 (d, J=5.8 Hz, 2H)

Example 5-60

Synthesis of N-benzyl-2-(3-chlorophenyl)oxazolo[5,4-b]pyridine-5-amine

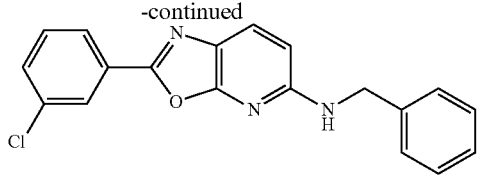

20 mg (0.1 mmol) of a target compound was obtained with a yield of about 23% in the same manner as in Example 5-30, except that 70 mg (0.3 mmol) of 5-chloro-2-(3-chlorophenyl)oxazolo[5,4-b]pyridine was used as a starting material.

$^1$H NMR (300 MHz, CDCl$_3$) δ 8.22 (s, 1H), 8.10-8.08 (m, 1H), 7.81 (d, J=8.6 Hz, 1H), 7.51-7.34 (m, 7H), 6.48 (d, J=8.6 Hz, 1H), 5.08 (s, 1H), 4.67 (d, J=5.6 Hz, 2H)

Example 5-61

Synthesis of N-benzyl-2-(4-chlorophenyl)oxazolo[5,4-b]pyridine-5-amine

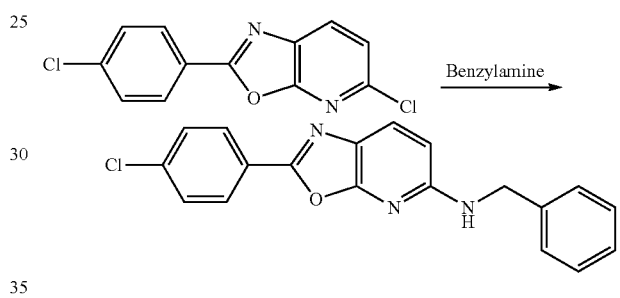

29 mg (0.09 mmol) of a target compound was obtained with a yield of about 32% in the same manner as in Example 5-30, except that 70 mg (0.3 mmol) of 5-chloro-2-(4-chlorophenyl)oxazolo[5,4-b]pyridine was used as a starting material.

$^1$H NMR (300 MHz, CDCl$_3$) δ 8.15 (d, J=8.8 Hz, 2H), 7.81 (d, J=8.6 Hz, 1H), 7.51 (d, J=8.8 Hz, 2H), 7.46-7.30 (m, 5H), 6.47 (d, J=8.6 Hz, 1H), 5.06 (s, 1H0, 4.67 (d, J=5.7 Hz, 2H)

Example 5-62

Synthesis of N-(2-morpholinoethyl)-2-phenylthiazolo[5,4-b]pyridine-5-amine

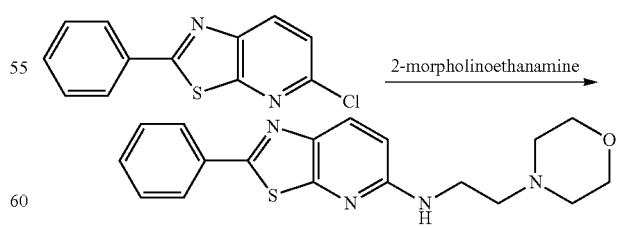

31 mg (0.1 mmol) of a target compound was obtained with a yield of about 50% in the same manner as in Example 5-30, except that 50 mg (0.2 mmol) of 5-chloro-2-phenylthiazolo[5,4-b]pyridine and 3 equivalents of 2-morpholinoethanamine were used as starting materials.

¹H NMR (300 MHz, CDCl₃) δ 8.05-8.00 (m, 3H), 7.54-7.47 (m, 3H), 6.59 (d, J=8.9 Hz, 1H), 5.38 (s, 1H), 3.78 (t, J=4.6 Hz, 4H), 3.52 (q, J=5.1 Hz, 2H), 2.69 (t, J=6.0 Hz, 2H), 2.55 (t, J=4.4 Hz, 4H)

Example 5-63

Synthesis of N-benzyl-N-methyl-2-phenyloxazolo[5,4-b]pyridine-5-amine

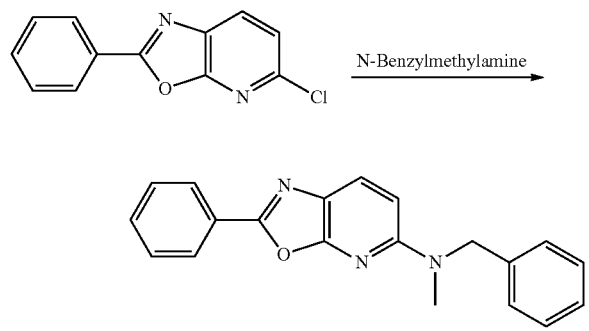

218 mg (0.7 mmol) of a target compound was obtained with a yield of about 80% in the same manner as in Example 5-30, except that 200 mg (0.9 mmol) of 5-chloro-2-phenyloxazolo[5,4-b]pyridine and 5 equivalents of N-benzylmethylamine were used as starting materials.

¹H NMR (300 MHz, CDCl₃) δ 8.25-8.21 (m, 2H), 7.85 (d, J=8.8 Hz, 1H), 7.54-7.50 (m, 3H), 7.39-7.27 (m, 5H), 6.58 (d, J=8.8 Hz, 1H), 4.91 (s, 2H), 3.21 (s, 3H)

Example 5-64

Synthesis of N-benzyl-N-methyl-2-phenylthiazole[5,4-b]pyridine-5-amine

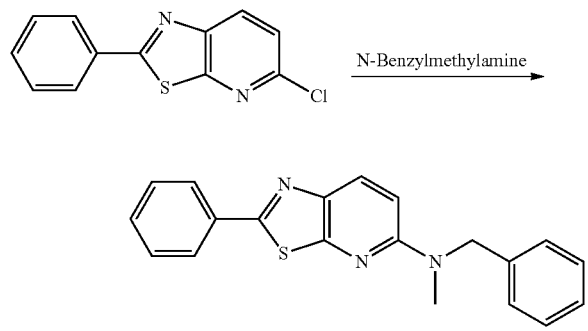 [SMILES: Clc1ccc2nc(-c3ccccc3)oc2n1 ; c1ccc(CNc2ccc3nc(-c4ccccc4)oc3n2)cc1]

100 mg (0.3 mmol) of a target compound was obtained with a yield of about 72% in the same manner as in Example 5-30, except that 100 mg (0.4 mmol) of 5-chloro-2-phenylthiazolo[5,4-b]pyridine was used as a starting material.

¹H NMR (300 MHz, CDCl₃) δ 8.05 (d, J=9.1 Hz, 3H), 7.54-7.47 (m, 3H), 7.40-7.29 (m, 5H), 6.71 (d, J=9.1 Hz, 1H), 4.93 (s, 2H), 3.21 (s, 3H)

Example 5-65

Synthesis of N-benzyl-2-(2-chlorophenyl)-N-methyloxazolo[5,4-b]pyridine-5-amine

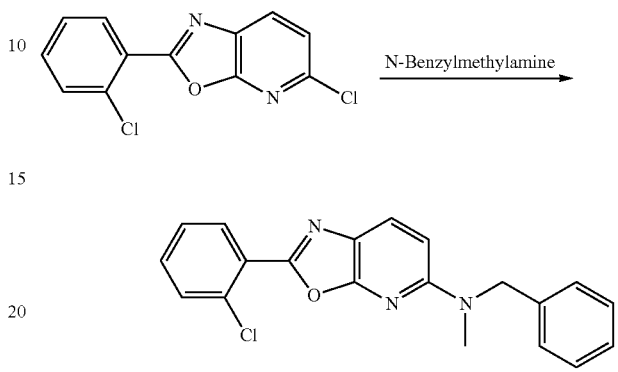

70 mg (0.2 mmol) of a target compound was obtained with a yield of about 67% in the same manner as in Example 5-30, except that 80 mg (0.3 mmol) of 5-chloro-2-(2-chlorophenyl)oxazolo[5,4-b]pyridine was used as a starting material.

¹H NMR (300 MHz, CDCl₃) δ 8.19-8.16 (m, 1H), 7.92 (d, J=8.8 Hz, 1H), 7.60-7.57 (m, 1H), 7.46-7.28 (m, 7H), 6.60 (d, J=8.9 Hz, 1H), 4.92 (s, 2H), 3.22 (s, 3H)

Example 5-66

Synthesis of N-benzyl-2-(3-fluorophenyl)-N-methyloxazolo[5,4-b]pyridine-5-amine

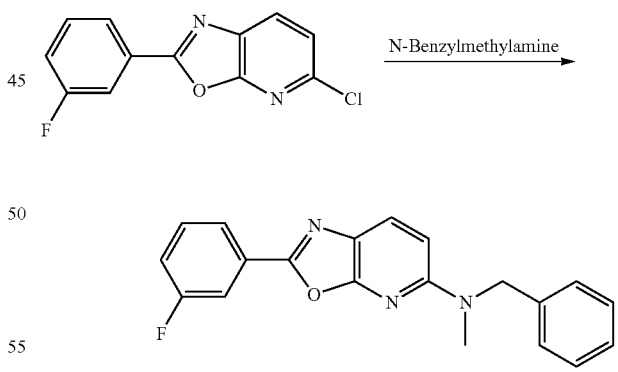

118 mg (0.4 mmol) of a target compound was obtained with a yield of about 98% in the same manner as in Example 5-30, except that 90 mg (0.4 mmol) of 5-chloro-2-(3-fluorophenyl)oxazolo[5,4-b]pyridine was used as a starting material.

¹H NMR (300 MHz, CDCl₃) δ 8.01 (d, J=7.8 Hz, 1H), 7.93 (d, J=5.6 Hz, 1H), 7.85 (d, J=8.8 Hz, 1H), 7.53-7.46 (m, 1H), 7.40-7.28 (m, 5H), 7.24-7.18 (m, 1H), 6.59 (d, J=8.8 Hz, 1H), 4.91 (s, 2H), 3.21 (s, 3H)

Example 5-67

Synthesis of N-benzyl-2-(3-chlorophenyl)-N-methyloxazolo[5,4-b]pyridine-5-amine

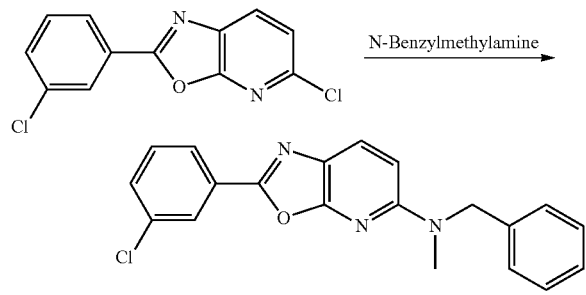

57 mg (0.2 mmol) of a target compound was obtained with a yield of about 65% in the same manner as in Example 5-30, except that 80 mg (0.3 mmol) of 5-chloro-2-(3-chlorophenyl)oxazolo[5,4-b]pyridine was used as a starting material.

$^1$H NMR (300 MHz, CDCl$_3$) δ 8.24-8.22 (m, 1H), 8.11-8.08 (m, 1H), 7.85 (d, J=8.8 Hz, 1H), 7.48-7.46 (m, 2H), 7.40-7.35 (m, 2H), 7.35-7.28 (m, 4H), 6.59 (d, J=8.9 Hz, 1H), 4.91 (s, 2H), 3.22 (s, 3H)

Example 5-68

Synthesis of N-benzyl-2-(4-chlorophenyl)-N-methyloxazolo[5,4-b]pyridine-5-amine

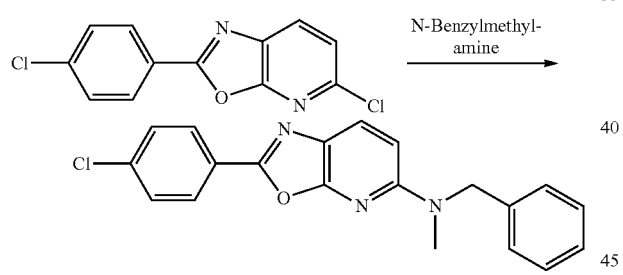

121 mg (0.3 mmol) of a target compound was obtained with a yield of about 92% in the same manner as in Example 5-30, except that 100 mg (0.4 mmol) of 5-chloro-2-(4-chlorophenyl)oxazolo[5,4-b]pyridine was used as a starting material.

$^1$H NMR (300 MHz, CDCl$_3$) δ 8.15 (d, J=8.6 Hz, 2H), 7.83 (d, J=8.8 Hz, 1H), 7.50 (d, J=8.6 Hz, 2H), 7.40-7.28 (m, 5H), 6.58 (d, J=8.8 Hz, 1H), 4.90 (s, 2H), 3.21 (s, 3H)

Example 5-69

Synthesis of N-benzyl-N-methyl-2-p-tolyloxazolo[5,4-b]pyridine-5-amine

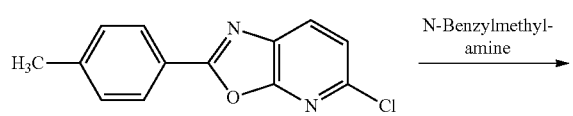

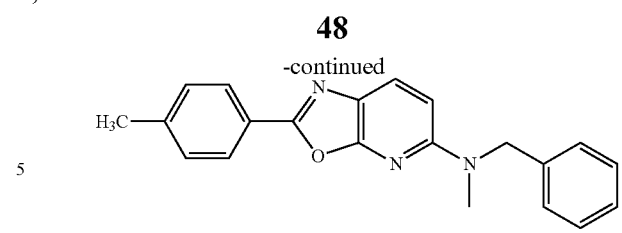

130 mg (60%) of a target compound was obtained with a yield of about 60% in the same manner as in Example 5-30, except that 172 mg (0.7 mmol) of 5-chloro-2-p-tolyloxazolo[5,4-b]pyridine was used as a starting material.

$^1$H NMR (300 MHz, CDCl$_3$) δ 8.12 (d, J=8.2 Hz, 2H), 7.83 (d, J=8.7 Hz, 1H), 7.39-7.28 (m, 7H), 6.56 (d, J=8.8 Hz, 1H), 4.90 (s, 2H), 3.21 (s, 3H), 2.46 (s, 3H)

Example 5-70

Synthesis of N-benzyl-2-(4-methoxyphenyl)-N-methyloxazolo[5,4-b]pyridine-5-amine

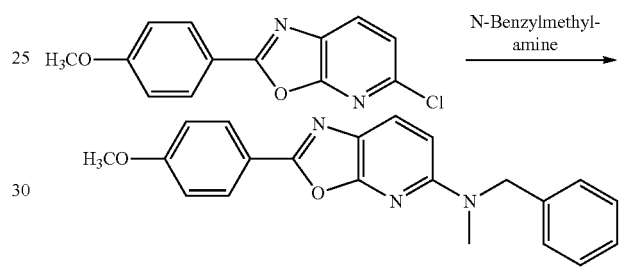

67 mg (0.2 mmol) of a target compound was obtained with a yield of about 57% in the same manner as in Example 5-30, except that 88 mg (0.3 mmol) of 5-chloro-2-(4-methoxyphenyl)oxazolo[5,4-b]pyridine was used as a starting material.

$^1$H NMR (300 MHz, CDCl$_3$) δ 8.17 (d, J=9.0 Hz, 2H0, 7.81 (d, J=8.7 Hz, 1H), 7.37-7.28 (m, 5H), 7.04 (d, J=6.9 Hz, 2H), 6.55 (d, J=8.8 Hz, 1H), 4.90 (s, 2H), 3.92 (s, 3H), 3.20 (s, 3H)

Example 5-71

Synthesis of N-benzyl-N-methyl-2-(4-nitrophenyl)oxazolo[5,4-b]pyridine-5-amine

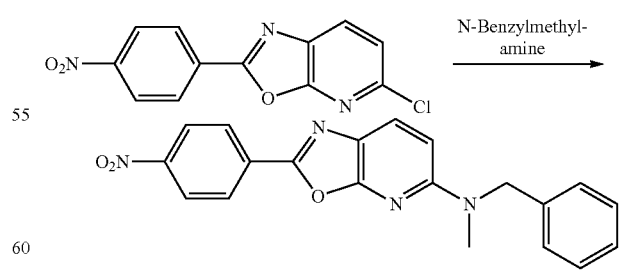

65 mg (0.2 mmol) of a target compound was obtained with a yield of about 99% in the same manner as in Example 5-30, except that 45 mg (0.2 mmol) of 5-chloro-2-(4-nitrophenyl)oxazolo[5,4-b]pyridine was used as a starting material.

¹H NMR (300 MHz, CDCl₃) δ 8.36 (s, 4H), 7.88 (d, J=8.9 Hz, 1H), 7.40-7.26 (m, 5H), 6.63 (d, J=8.9 Hz, 1H), 4.92 (s, 2H), 3.24 (s, 3H)

Example 5-72

Synthesis of 4-(5-benzyl(methyl)amino)oxazolo[5,4-b]pyridine-2-yl)benzonitrile

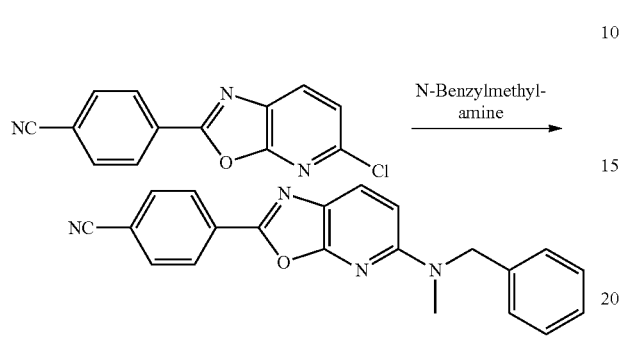

61 mg (0.2 mmol) of a target compound was obtained with a yield of about 71% in the same manner as in Example 5-30, except that 63 mg (0.3 mmol) of 4-(5-chlorooxazolo[5,4-b]pyridine-2-yl)benzonitrile was used as a starting material.

¹H NMR (300 MHz, CDCl₃) δ 8.30 (d, J=8.4 Hz, 2H0, 7.88-7.28 (m, 3H), 7.40-7.28 (m, 5H), 6.62 (d, J=8.9 Hz, 1H), 4.92 (s, 2H), 3.23 (s, 3H)

Example 5-73

Synthesis of N-methyl-2-phenyloxazolo[5,4-b]pyridine-5-amine

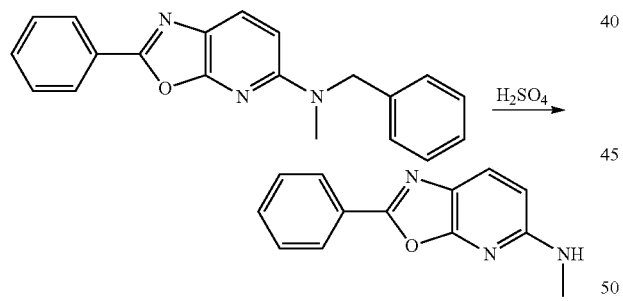

50 mg (0.16 mmol) of N-benzyl-N-methyl-2-phenyloxazolo[5,4-b]pyridine-5-amine and 0.25 ml of 95% H₂SO₄ were mixed together by stirring for about 12 hours. Termination of the reaction was confirmed by TLC, and the reaction product was cooled to room temperature, followed by dropwise addition of 1.25 ml of H2O. The reaction product was titrated using a 15% NaOH solution to a pH 4. After a resulting solid was filtrated, a resulting filtrate was titrated to a pH 10. An aqueous phase was separated with methylene chloride, followed by distillation under reduced pressure to obtain 25 mg (0.1 mmol) of a target compound with a yield of about 69%.

¹H NMR (300 MHz, CDCl₃) δ 8.24-8.20 (m, 2H0, 7.83 (d, J=8.6 Hz, 1H), 7.55-7.51 (m, 3H), 6.46 (d, J=8.6 Hz, 1H0, 4.75 (s, 1H), 3.07 (d, J=5.1 Hz, 3H)

Example 5-74

Synthesis of N-methyl-2-phenylthiazolo[5,4-b]pyridine-5-amine

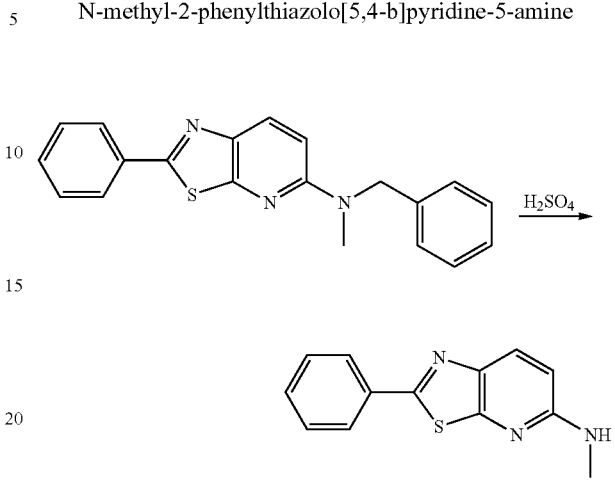

47 mg (0.2 mmol) of a target compound was obtained with a yield of about 92% in the same manner as in Example 5-73, except that 70 mg (0.2 mmol) of N-benzyl-N-methyl-2-phenylthiazolo[5,4-b]pyridine-5-amine was used as a starting material.

¹H NMR (300 MHz, CDCl₃) δ 8.05-8.01 (m, 3H), 7.52-7.48 (m, 3H), 6.56 (d, J=8.9 Hz, 1H), 4.87 (s, 1H), 3.06 (d, J=5.1 Hz, 3H)

Example 5-75

Synthesis of 2-(3-fluorophenyl)-N-methyloxazolo[5,4-b]pyridine-5-amine

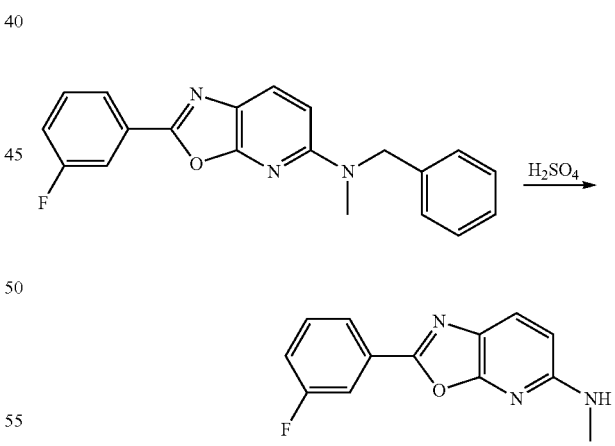

31 mg (0.1 mmol) of a target compound was obtained with a yield of about 58% in the same manner as in Example 5-73, except that 70 mg (0.2 mmol) of N-benzyl-2-(3-fluorophenyl)-N-methyloxazolo[5,4-b]pyridine-5-amine was used as a starting material.

¹H NMR (300 MHz, CDCl₃) δ 8.00 (d, J=5.4 Hz, 1H), 7.90 (d, J=5.6 Hz, 1H), 7.83 (d, J=8.6 Hz, 1H), 7.54-7.47 (m, 1H), 7.25-7.18 (m, 1H), 6.47 (d, J=8.6 Hz, 1H), 4.79 (s, 1H), 3.07 (d, J=5.1 Hz, 3H)

Example 5-76

Synthesis of 2-(3-chlorophenyl)-N-methyloxazolo[5,4-b]pyridine-5-amine

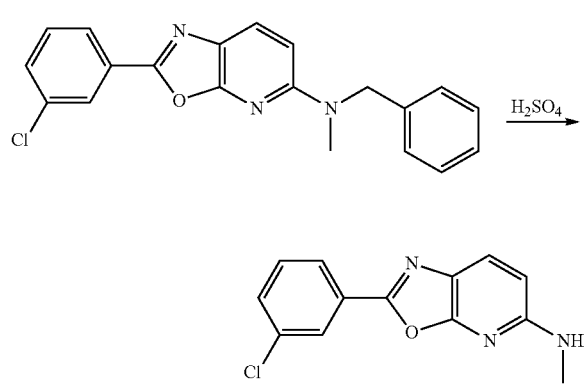

30 mg (0.1 mmol) of a target compound was obtained with a yield of about 72% in the same manner as in Example 5-73, except that 57 mg (0.2 mmol) of N-benzyl-2-(3-chlorophenyl)-N-methyloxazolo[5,4-b]pyridine-5-amine was used as a starting material.

$^1$H NMR (300 MHz, CDCl$_3$) δ 8.22 (s, 1H), 8.10-8.07 (m, 1H), 7.82 (d, J=8.6 Hz, 1H), 7.50-7.43 (m, 2H), 6.47 (d, J=8.6 Hz, 1H), 4.79 (s, 1H), 3.08 (d, J=5.1 Hz, 3H)

Example 5-77

Synthesis of 2-(4-chlorophenyl)-N-methyloxazolo[5,4-b]pyridine-5-amine

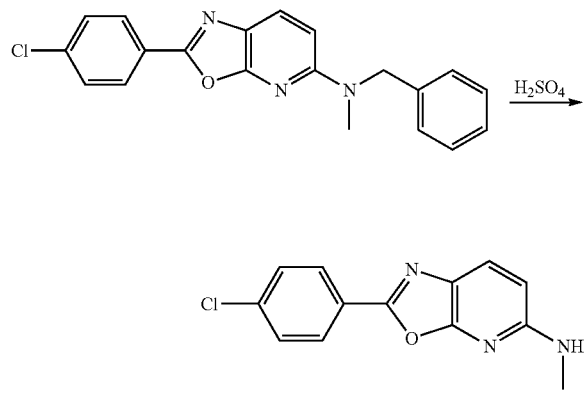

43 mg (0.2 mmol) of a target compound was obtained with a yield of about 83% in the same manner as in Example 5-73, except that 70 mg (0.2 mmol) of N-benzyl-2-(4-chlorophenyl)-N-methyloxazolo[5,4-b]pyridine-5-amine was used as a starting material.

$^1$H NMR (300 MHz, CDCl$_3$) δ 8.13 (d, J=8.6 Hz, 2H), 7.80 (d, J=8.6 Hz, 1H), 7.50 (d, J=8.6 Hz, 2H), 6.45 (d, J=8.6 Hz, 1H), 4.78 (s, 1H), 3.06 (d, J=5.1 Hz, 3H)

Example 5-78

Synthesis of N-methyl-2-p-tolyloxazolo[5,4-b]pyridine-5-amine

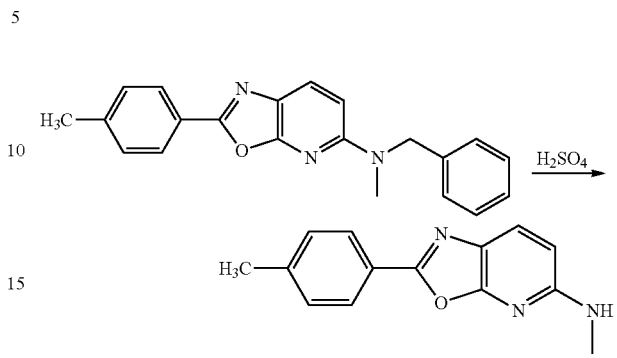

21 mg (0.09 mmol) of a target compound was obtained with a yield of about 75% in the same manner as in Example 5-73, except that 40 mg (0.12 mmol) of N-benzyl-N-methyl-2-p-tolyloxazolo[5,4-b]pyridine-5-amine was used as a starting material.

$^1$H NMR (300 MHz, CDCl$_3$) δ 8.09 (d, J=7.6 Hz, 2H), 7.79 (d, J=8.5 Hz, 1H), 7.32 (d, J=7.8 Hz, 2H), 6.42 (d, J=8.4 Hz, 1H), 3.04 (s, 3H), 2.44 (s, 3H)

Example 5-79

Synthesis of 2-(4-methoxyphenyl)-N-methyloxazolo[5,4-b]pyridine-5-amine

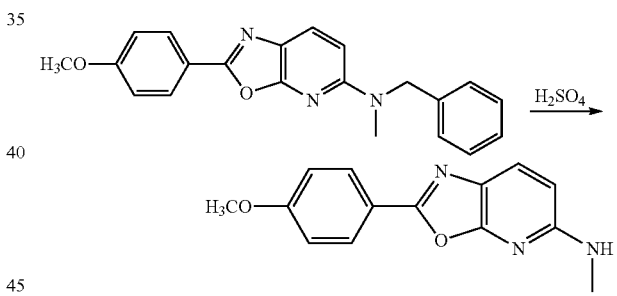

18 mg (0.07 mmol) of a target compound was obtained with a yield of about 60% in the same manner as in Example 5-73, except that 40 mg (0.12 mmol) of N-benzyl-2-(4-methoxyphenyl)-N-methyloxazolo[5,4-b]pyridine-5-amine was used as a starting material.

$^1$H NMR (300 MHz, CDCl$_3$) δ 8.14 (d, J=9.0 Hz, 2H), 7.77 (d, J=8.5 Hz, 1H), 7.03 (d, J=9.0 Hz, 2H), 6.42 (d, J=8.6 Hz, 1H), 3.90 (s, 3H), 3.04 (d, J=5.1 Hz, 3H)

Example 5-80

Synthesis of N-cyclohexyl-2-phenyloxazolo[5,6-b]pyridine-5-amine

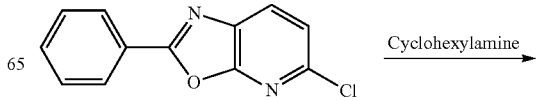

-continued

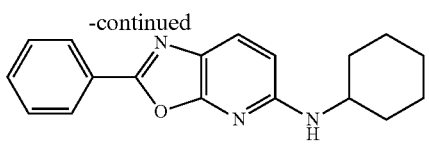

20 mg (0.07 mmol) of a target compound was obtained with a yield of about 34% in the same manner as in Example 5-30, except that 50 mg (0.2 mmol) of 5-chloro-2-phenyloxazolo[5,4-b]pyridine and 10 equivalents of cyclopentylamine were used as starting materials.

$^1$H NMR (300 MHz, MeOD) δ 8.12-8.11 (m, 2H), 7.70 (d, J=8.7 Hz, 1H), 7.57-7.53 (m, 3H), 6.54 (d, J=8.7 Hz, 1H), 3.79 (s, 1H), 2.08 (d, J=12.2 Hz, 2H), 1.83 (dd, J=3.9, 5.7 Hz, 2H), 1.71 (d, J=13.2 Hz, 1H), 1.52-1.42 (m, 2H), 1.30 (t, J=12.0 Hz, 3H)

Example 6

Screening of MAO-B's Activity Inhibitory Material

Whether the compounds of Example 5 inhibit activity of MAO-B was tested.

A stock solution was prepared using a human MAO-B enzyme (purchased from Aldrich) and a Amplex® Red monoamine oxidase assay kit according to a preparation manual. The kit includes a 5× reaction buffer, an Amplex® red reagent (1 mg), HRP, DMSO, $H_2O_2$, p-tyramine (substrate of MAO-A, B), benzylamine (substrate of MAO-B), clorgiline (inhibitor of MAO-A), and pargyline (inhibitor of MAO-B). Among these reagents in the kit, benzylamine was used as a substrate for MAO-B, and pargyline was used as an MAO-B inhibitor. A solution as overall substrates was prepared as follows. 200 ul of a solution of 1 mg of Amplex® red sufficiently dissolved in 200 ul of DMSO, 100 ul of a mixed solution of HRP and 1 ml of a 1× buffer, 200 ul of a solution of benzylamine dissolved in 1.2 ml of $dH_2O$ were added to 9.5 ml of a 1× buffer to reach a total volume of 10 mL, which is sufficient for 100 wells. 0.5 ul of a mixture of MAO-B inhibitor pargyline and 1 ml of $dH_2O$ was put into each well. First, the activity of MAO-B was determined using 10 uM of the synthesized compound.

96 wells were injected with positive and negative types, and the wile type. The positive type included only substrate and hydrogen peroxide, and the negative type included only substrate. For the wild type, corresponding wells were injected with the enzyme, substrate, and MAO-B inhibitor, but with no synthesized compound. Afterward, 2 ul of the synthesized compound (1 mM) was added into each well, and the human MAO-B enzyme was put only into the $1^{st}$ row of wells. 0.5 ug of the human MAO-B was put into each well along with 100 ul of a 1× buffer. The human MAO-B enzyme was put into the $2^{nd}$ row of the wells along with 0.5 ul of a pargyline, the MAO-B inhibitor. To reduce an experimental error for accuracy, the test was repeated three times for each compound. After 30 minutes, 100 ul of the substrate solution was added into each well in a darkroom. The test was performed in the darkroom due to light sensitivity of the Amplex® reagent. Finally, a total volume of the reaction solution per well reached 200 ul. After about 2 to 3 hours, chromophoric degrees of the samples were measured. A variation in data values for the $1^{st}$ and $2^{nd}$ rows of the wells indicates the pure reaction activity of the MAO-B enzyme with the substrate. Using the samples with the synthesized compound the remaining activity of MAO-B after inhibited by the synthesized compound may be determined. This is because the activities of the other enzymes excluding the MAO-B enzyme may be excluded through this method. Compounds with high inhibitory activity at a concentration of 10 uM were screened from among the synthesized compounds at a compound concentration of 10 uM. Afterward, concentration-dependent $IC_{50}$ values of these compounds may be obtained through an activity assay at different concentrations of 0.001 uM, 0.01 uM, 0.1 uM, 1 uM, and 10 uM.

The results of the test on whether the compounds of Example 5 inhibited the activity of MAO-B are shown in Table 1 below.

TABLE 1

| Compound | Remaining activity of MAO-B (%) | $IC_{50}(\mu M)$ |
|---|---|---|
| Example 5-30 | 2.31 | 0.41 |
| Example 5-31 | 1.7 | 7.3 |
| Example 5-32 | 7.7 | 111.9 |
| Example 5-33 | 14.2 | 16.3 |
| Example 5-34 | 8.4 | 8.7 |
| Example 5-35 | 42.4 | — |
| Example 5-36 | 33.5 | — |
| Example 5-37 | 3.09 | 2 |
| Example 5-38 | 1.8 | 8.3 |
| Example 5-39 | 0.6 | 13.2 |
| Example 5-40 | 13.8 | 0.27 |
| Example 5-41 | 17 | 38.4 |
| Example 5-42 | −7.8 | — |
| Example 5-43 | −21.5 | — |
| Example 5-44 | 10.1 | — |
| Example 5-45 | 26.5 | 10.1 |
| Example 5-46 | 56.0 | — |
| Example 5-47 | 28.6 | 0.096 |
| Example 5-48 | 46.2 | — |
| Example 5-49 | 15.8 | 1.52 |
| Example 5-50 | 71.2 | — |
| Example 5-51 | 37.2 | — |
| Example 5-52 | 43 | — |
| Example 5-53 | 39.3 | — |
| Example 5-54 | 57.5 | — |
| Example 5-55 | −1.8 | — |
| Example 5-56 | 61.4 | — |
| Example 5-57 | 63.1 | — |
| Example 5-58 | 60.8 | $1.9 \times 10^3$ |
| Example 5-59 | 51.9 | — |
| Example 5-60 | 55.4 | — |
| Example 5-61 | 46.4 | — |
| Example 5-62 | 42.7 | — |
| Example 5-63 | 53.2 | $5.2 \times 10^4$ |
| Example 5-64 | 47.8 | — |
| Example 5-65 | 84.1 | — |
| Example 5-66 | 43 | — |
| Example 5-67 | 47.3 | 68.2 |
| Example 5-68 | 24.1 | 5.08 |
| Example 5-69 | 84.1 | — |
| Example 5-70 | 52.4 | — |
| Example 5-71 | 101.2 | — |
| Example 5-72 | 108.8 | — |
| Example 5-73 | 51 | — |
| Example 5-74 | 27.2 | 15.7 |
| Example 5-75 | 22 | 9.86 |
| Example 5-76 | 4.4 | 2.99 |
| Example 5-77 | 4.14 | 3.02 |
| Example 5-78 | 45.8 | — |
| Example 5-79 | 84.5 | — |
| Example 5-80 | 11.1 | 8.72 |
| Selegiline | 0.1 | 9.7 |

As described above, a method according to the one or more embodiments of the present disclosure may effectively screen a prophylactic or therapeutic candidate material for preventing or treating a degenerative brain disease. A variety of degenerative brain diseases may be effectively prevented or treated with pharmaceutical composition including the screened prophylactic or therapeutic candidate material.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

What is claimed is:

1. A method for treating a degenerative brain disease, the method comprising administering to a subject in need thereof an effective amount of a pharmaceutical composition comprising a compound represented by Formula 1 below, a pharmaceutically acceptable salt, an isomer, a solvate, a hydrate, or a combination thereof,

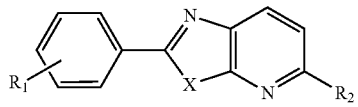

Formula I wherein, in Formula 1 above, $R_1$ and $R_2$ are each independently a hydrogen atom, a halogen atom, a nitro group, a cyano group, a carboxyl group, a hydroxyl group, a substituted or unsubstituted $C_1$-$C_{12}$ alkyl group, a substituted or unsubstituted $C_2$-$C_{12}$ alkenyl group, a substituted or unsubstituted $C_2$-$C_{12}$ alkynyl group, a substituted or unsubstituted $C_3$-$C_{15}$ cycloalkyl group, a substituted or unsubstituted $C_3$-$C_{40}$ heterocycloalkyl group, (a substituted or unsubstituted $C_6$-$C_{20}$ aryl) $C_1$-$C_{12}$ alkyl group, a substituted or unsubstituted $C_1$-$C_{12}$ alkoxy group, a substituted or unsubstituted $C_6$-$C_{20}$ arylamine group, a substituted or unsubstituted $C_6$-$C_{30}$ diarylamine group, a substituted or unsubstituted $C_6$-$C_{20}$ aryloxy group, a substituted or unsubstituted $C_6$-$C_{20}$ aryl group, or a substituted or unsubstituted $C_5$-$C_{20}$ heteroaryl group; and X is —O—, —S—, or —N(H)—, and the compound represented by Formula 1 is at least one of N-cyclohexyl-2-phenyloxazolo[5,4-b]pyridine-5-amine, 2-phenyl-5-(pyrrolidine-1-yl)thiazolo[5,4-b]pyridine, 2-(2-chlorophenyl)-5-(pyrrolidine-1-yl)oxazolo[5,4-b]pyridine, 2-(3-chlorophenyl)-5-(pyrrolidine-1-yl)oxazolo[5,4-b]pyridine, 2-(4-fluorophenyl)-5-(pyrrolidine-1-yl)oxazolo[5,4-b]pyridine, 2-phenyl-5-(piperidine-1-yl)oxazolo[5,4-b]pyridine, 2-phenyl-5-(piperidine-1-yl)thiazolo[5,4-b]pyridine, 2-(2-chlorophenyl)-5-(piperidine-1-yl)oxazolo[5,4-b]pyridine, 2-(3-fluorophenyl)-5-(piperidine-1-yl)oxazolo[5,4-b]pyridine, 2-(3-chlorophenyl)-5-(piperidine-1-yl)oxazolo[5,4-b]pyridine, 3-(5-(piperidine-1-yl)oxazolo[5,4-b]pyridine-2-yl)benzonitrile, 2-(4-fluorophenyl)-5-(piperidine-1-yl)oxazolo[5,4-b]pyridine, 2-(4-bromophenyl)-5-(piperidine-1-yl)oxazolo[5,4-b]pyridine, 2-(3-chlorophenyl)-N-methyloxazolo[5,4-b]pyridine-5-amine, or 2-(4-chlorophenyl)-N-methyloxazolo[5,4-b]pyridine-5-amine.

2. The method of claim 1, wherein the degenerative brain disease is selected from the group consisting of Alzheimer's disease, mild cognitive impairment, vascular dementia, frontotemporal dementia, Louis corpuscle dementia, Creutzfeld-Jakob disease, traumatic head injuries, syphilis, acquired immune deficiency syndrome (AIDS), viral infection, brain abscess, brain tumor, dementia in metabolic disease, hypoxia, Parkinson's disease, Huntington's disease, Pick's disease, epilepsy, ischemia, stroke, attention deficit hyperactivity disorder (ADHD), schizophrenia, depression, manic-depression, and stress disorder.

* * * * *